US012502538B2

(12) United States Patent
Fritzsche et al.

(10) Patent No.: US 12,502,538 B2
(45) Date of Patent: Dec. 23, 2025

(54) ELECTROACOUSTIC TRANSDUCER FOR IMPLANTATION IN AN EAR, METHOD FOR PRODUCING SUCH, AND COCHLEAR IMPLANT SYSTEM

(71) Applicants: Vibrosonic GmbH, Mannheim (DE); MED-EL ELEKTROMEDIZINISCHE GERÄTE GMBH, Innsbruck (AT)

(72) Inventors: Tobias Fritzsche, Ludwigshafen (DE); Dominik Kaltenbacher, Mannheim (DE); Jonathan Schächtele, Mannheim (DE); Florian Strobl, Heddesheim (DE); Martin Theuring, Mannheim (DE); Daniela Wildenstein, Tübingen (DE); Daniel Schurzig, Hannover (DE); Roland Hessler, Innsbruck (AT)

(73) Assignees: MED-EL ELEK TROMEDIZINISCHE GERÄTE GMBH, Innsbruck (AT); Vibrosonic GmbH, Mannheim (DE)

( * ) Notice: Subject to any disclaimer, the term of this patent is extended or adjusted under 35 U.S.C. 154(b) by 1134 days.

(21) Appl. No.: 17/309,468

(22) PCT Filed: Nov. 29, 2019

(86) PCT No.: PCT/EP2019/083154
§ 371 (c)(1),
(2) Date: May 28, 2021

(87) PCT Pub. No.: WO2020/109590
PCT Pub. Date: Jun. 4, 2020

(65) Prior Publication Data
US 2022/0023632 A1 Jan. 27, 2022

(30) Foreign Application Priority Data
Nov. 30, 2018 (DE) ..................... 10 2018 220 731.3

(51) Int. Cl.
*H04R 25/00* (2006.01)
*A61N 1/36* (2006.01)

(52) U.S. Cl.
CPC ....... *A61N 1/36038* (2017.08); *H04R 25/606* (2013.01); *H04R 25/65* (2013.01); *H04R 25/602* (2013.01)

(58) Field of Classification Search
CPC .......................... H04R 25/606; A61N 1/36038
(Continued)

(56) References Cited

U.S. PATENT DOCUMENTS 6,259,951 B1 7/2001 Kuzma et al.
6,422,991 B1 * 7/2002 Jaeger ................. H04R 25/606 600/25
(Continued)

FOREIGN PATENT DOCUMENTS

DE 102005017493 10/2006
DE 102010009453 9/2011
(Continued)

OTHER PUBLICATIONS

English Translation of Schachtele et al. WO-2016124465 (Year: 2016).*
(Continued)

*Primary Examiner* — Katherine A Faley
(74) *Attorney, Agent, or Firm* — Schwegman Lundberg & Woessner, P.A.

(57) ABSTRACT

In order to use the residual hearing in patients indicated for a cochlear implant (CI), it is advantageous to supplement the electrical stimulation of the cochlear implant with an acoustic stimulation. Such residual hearing is usually present in a frequency range below one kilohertz.

19 Claims, 13 Drawing Sheets

(58) Field of Classification Search
USPC .......................................................... 381/328
See application file for complete search history.

(56) References Cited

U.S. PATENT DOCUMENTS

| | | | | |
|---|---|---|---|---|
| 9,999,770 | B2 | 6/2018 | Walraevens et al. | |
| 2010/0324355 | A1* | 12/2010 | Spitaels | H04R 25/606 607/57 |
| 2011/0029031 | A1 | 2/2011 | Parker | |
| 2015/0126900 | A1 | 5/2015 | Walraevens et al. | |
| 2021/0128907 | A1* | 5/2021 | Patnala | A61N 1/0541 |

FOREIGN PATENT DOCUMENTS

| | | | | |
|---|---|---|---|---|
| DE | 102015101482 | | 5/2016 | |
| WO | WO-2004024212 | A2 | 3/2004 | |
| WO | WO-2016124465 | A1 * | 8/2016 | A61N 1/0541 |

OTHER PUBLICATIONS

"International Application Serial No. PCT/EP2019/083154, International Search Report mailed Jan. 31, 2020", w/ English Translation, (Jan. 31, 2020), 5 pgs.
"International Application Serial No. PCT EP2019 083154, Written Opinion mailed Jan. 31, 2020", w Concise Statement of Relevance, (Jan. 31, 2020), 8 pgs.
"European Application No. 19186572.2, Office Action dated May 8, 2025", w English Translation, (May 8, 2025), 12 pgs.

* cited by examiner

ELECTROACOUSTIC TRANSDUCER FOR IMPLANTATION IN AN EAR, METHOD FOR PRODUCING SUCH, AND COCHLEAR IMPLANT SYSTEM

PRIORITY APPLICATIONS

This application is a U.S. National Stage Filing under 35 U.S.C. § 371 from International Application No. PCT/EP2019/083154, filed on Nov. 29, 2019, and published as WO2020/109590 on Jun. 4, 2020, which claims the benefit of priority to German Application No. 10 2018 220 731.3, filed on Nov. 30, 2018; the benefit of priority of each of which is hereby claimed herein, and which applications and publication are hereby incorporated herein by reference in their entirety.

In order to use the residual hearing in patients indicated for a cochlear implant (CI), it is advantageous to supplement the electrical stimulation of the cochlear implant with an acoustic stimulation. Such residual hearing is usually present in a frequency range below one kilohertz.

In the prior art, there are a number of ways to use residual hearing. For example, a cochlear implant can be combined with a classic hearing aid. However, the known limitations of such hearing aids with regard to visibility, the limited amplification due to feedback etc. come into play. Another option is to supplement the cochlear implant with an active middle ear implant, i.e., an implanted acoustic hearing aid. However, this considerably increases the surgical expense.

Figure 12:
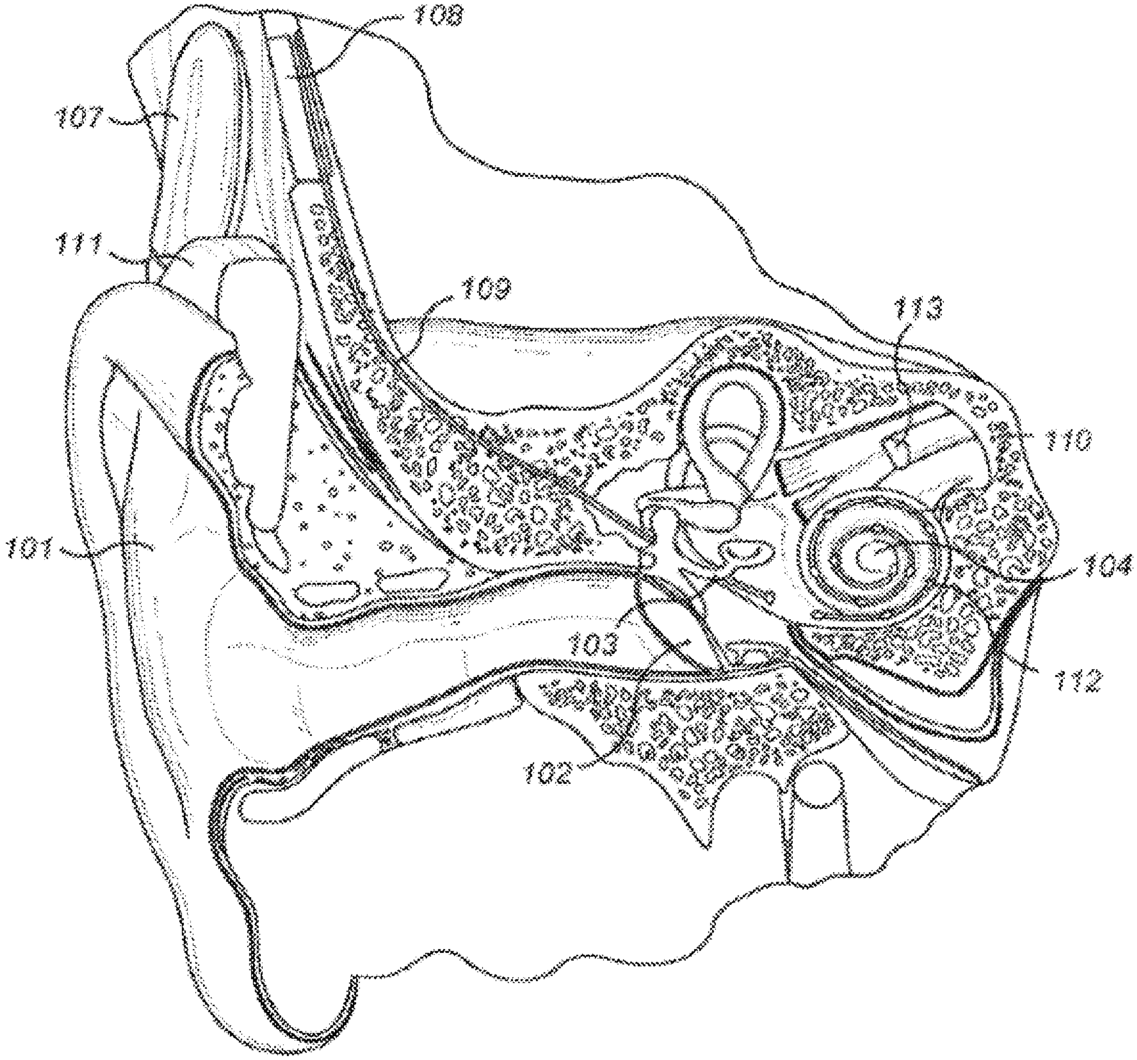

A naturally functioning ear transmits sounds, as shown in FIG. 12, through outer ear 101 to eardrum 102, which oscillates the ossicles of middle ear 103 (malleus, incus, and stapes). The stapes footplate is positioned in the oval window, which forms the one interface to the fluid-filled inner ear (the cochlea) 104. The round window forms the other interface between the middle ear and inner ear. By moving the stapes, a pressure wave is generated in cochlea 104, which stimulates the sensory cells of the hearing system (hair cells). Cochlea 104 is a long, narrow passage that spirally winds around its central axis (called the modiolus) for about two and a half turns. Cochlea 104 comprises an upper channel known as the scala vestibuli, a middle channel known as the scala media, and a lower channel known as the scala tympani. The hair cells connect to the spiral ganglion cells of cochlear nerve 113 which are located in the modiolus. In response to received tones, which are transferred from middle ear 103, fluid-filled cochlea 104 acts as a transducer to generate electrical pulses which are transmitted to cochlear nerve 113 and ultimately to the brain.

Hearing is impaired when there are problems with the ability to convert external sounds into meaningful action potentials along the neural substrate of cochlea 104. Hearing prostheses were developed to improve impaired hearing. If the impairment is connected to the function of middle ear 103, then a conventional hearing aid or a middle ear implant may be used to acoustically-mechanically stimulate the acoustic system in the form of amplified sound. Or if the impairment is associated with cochlea 104, then a cochlear implant with one or more implanted stimulation electrodes may electrically stimulate auditory nerve tissue with small currents provided by multiple electrode contacts distributed along the electrode.

FIG. 12 also shows some components of a typical cochlear implant system according to the prior art, including an external (i.e., non-implanted) microphone which provides an audio signal input for an external signal processor 111, in which various signal processing schemes may be implemented. A battery, which supplies the system with energy, is usually likewise located in an external component of the cochlear implant system. However, all of these components may also be implanted individually or all together. The processed signal is then (in the case it was generated in a non-implanted unit) converted into a digital data format, for example into a sequence of data words, for transmission into implant 108. In addition to processing the audio information in control electronics, hermetically sealed implant 108 also carries out additional signal processing, such as error correction, pulse formation, etc., and generates a stimulation pattern (based on the extracted audio information), which is sent through an electrode lead 109 to an implanted electrode arrangement on an electrode carrier 110.

Electrode carrier 110 typically comprises a plurality of electrode contacts 112 on its surface, which provide a selective stimulation of cochlea 104. Electrode contacts 112 are electrically connected to power sources in implant 108. Depending on context, electrode contacts 112 are also designated as electrode channels. Currently, relatively few electrode channels in cochlear implants are assigned to relatively broad frequency bands, wherein each electrode contact 112 addresses a group of neurons with an electrical stimulation pulse, which has a charge which is derived from the instantaneous amplitude of the signal envelope within this frequency band.

It is the object of the present invention to provide an electroacoustic transducer for implantation in the ear, which is able to be contacted with the inside of the inner ear or the cochlea and is preferably combinable with an electrode carrier which is insertable into the cochlea.

The problem is solved by the electroacoustic transducer, the method for producing an electroacoustic transducer, and the cochlear implant system. The respective dependent claims specify advantageous refinements of the electroacoustic transducer according to the invention and of the method according to the invention for producing an electroacoustic transducer.

In one embodiment of the invention, an electroacoustic transducer is specified which is suited for implantation into an ear of a person. In this embodiment of the invention, the electroacoustic transducer has an inner ear housing, at least one sound transducer and a middle ear component. The inner ear housing thereby surrounds an area adjacent to the sound transducer, which is subsequently designated as the inner ear area. The inner ear area may thus be considered the interior of the inner ear housing. According to the invention, the inner ear area is delimited by the sound transducer in this embodiment. The inner ear area is thus preferably surrounded by the inner ear housing together with the sound transducer, wherein the inner ear housing preferably has an open area in which the sound transducer may be arranged.

In this embodiment of the invention, the middle ear component is arranged on a side of the sound transducer opposite the inner ear area. Reference is made to the fact that it is conceivable that the middle ear component is arranged on the same side of the sound transducer as in the inner ear area, wherein, however, the previously described opposite arrangement is considered to be advantageous. It is thus advantageous if the sound transducer is arranged between the middle ear component and the inner ear area.

In this embodiment of the invention, the inner ear housing has at least one sound transmission window, which is incorporated into at least one wall of the inner ear housing, and through which vibrations are transmittable. Therefore, that opening, in which the sound transducer is arranged, is preferably not to be viewed as this type of sound transmission window. The sound transmission window is thus preferably incorporated in a wall of the inner ear housing in which the sound transducer is not arranged. Insofar as the aforementioned sound transmission window is arranged in the same wall of the inner ear housing as the sound transducer in one embodiment, then the sound transducer should preferably not be arranged in the sound transmission window.

That vibrations are transmittable by the sound transmission window means preferably that pressure vibrations and/or sound vibrations are transmittable by the sound transmission window. Whether the vibrations transmittable by the sound transmission window are considered to be pressure or sound vibration is merely a question of definition, which is also handled differently in the literature, depending on the wavelengths of the transmitted vibrations. The vibrations are preferably transmittable by the sound transmission window from the inner ear area to the outer area outside of the inner ear housing and/or from the outer area into the inner ear area.

In the embodiment of the invention described here, the inner ear housing is dimensioned so that it is insertable into an opening between a middle ear and an inner ear of a person, namely configured so that the inner ear area projects at least partially into the inner ear so that the at least one sound transmission window is located in the inner ear. For example, the inner ear housing may be inserted in this way into a round or oval window, or into an artificially created window between the middle ear and the inner ear of the person.

If the electroacoustic transducer according to the invention is provided to be inserted into a natural window, thus the oval or round window, then the corresponding dimensions may be selected using the dimensions of the specific patient, who receives the electroacoustic transducer, or they may be calculated from average dimensions of the corresponding window of adult persons or persons belonging to the corresponding age range. This also applies for all other dimensions described here.

In one advantageous embodiment of the invention, an opening between a middle ear and an inner ear of a person forms an intended position for the electroacoustic transducer. In one advantageous embodiment, the electroacoustic transducer is located in an intended position, if the at least one sound transmission window is located in the inner ear, as described above.

In one advantageous embodiment of the invention, the inner ear area and the middle ear area may be configured so that the mechanical impedance of the inner ear area is larger than the mechanical impedance of the middle ear area. This preferably applies at least in a frequency range which humans can hear, thus preferably between 20 Hz and 20 kHz. This feature may be provided for the electroacoustic transducer in and of itself; however, it is advantageous if the electroacoustic transducer is designed so that this condition is present in the state of being inserted into the ear. This may also be advantageously achieved in that optional housings of the inner ear area and/or of the middle ear area have different geometries and/or different sizes, and/or that windows with different geometries and/or sizes are provided in the corresponding housings, and/or that the inner ear area and the middle ear area have different materials and/or material combinations, and/or that the inner ear area and the middle ear area are filled with a medium at different volume proportions.

The sound transducer may advantageously be a device by means of which electrical signals are convertible into mechanical vibrations. However, it is also possible that the sound transducer is equipped to convert mechanical vibrations into electrical signals. In many embodiments of sound transducers, both possibilities are automatically realized by design.

In another embodiment of the invention, an electroacoustic transducer for implantation into an ear is specified, which has an inner ear housing, at least one sound transducer, and an electrode carrier.

In this embodiment according to the invention, the electrode carrier has one or more electrodes, which are arranged on a surface of the electrode carrier. The electrodes are thereby preferably arranged so that they may be externally electrically contacted (thus from outside the electrode carrier). The electrodes are thus preferably exposed on the surface of the electrode carrier. In this way, they may be physically and/or electrically bought into contact with a basilar membrane or a perilymph in the inner ear. In one preferred embodiment of the invention, the electrode carrier may be elongated. That the electrode carrier is elongated thereby means that it is extended longer in one direction, designated as the longitudinal direction, than in directions perpendicular thereto. The electrode carrier is preferably dimensioned so that it is insertable into a cochlea of a person. It thereby preferably assumes substantially the shape of a cylinder, an elongated cone, or a combination of the two in sections, such that it has a longitudinal axis defined by the cylindrical and/or conical axes in the extended state.

In one embodiment of the invention, the electroacoustic transducer may be embedded into the electrode carrier. In one specific embodiment, the transducer may thereby be embedded so that a longitudinal axis of the transducer is parallel to a longitudinal axis of the electrode carrier. An embodiment is particularly preferred, in which these two longitudinal axes are coaxial.

In another advantageous embodiment, the electroacoustic transducer may be embedded at a point along the longitudinal direction of the electrode carrier, which is located at an opening between a middle ear and an inner ear of a person, after the electrode carrier has been inserted into the inner ear of a person. In particular, it may thereby assume a position which is an intended position as described above.

In this case as well, the inner ear housing surrounds an inner ear area which is delimited by the sound transducer. That which was stated above regarding the first embodiment of the invention analogously applies with respect to the inner ear housing.

In this embodiment as well, the inner ear housing has at least one sound transmission window, which is incorporated into at least one wall of the inner ear housing, and through which vibrations are transmittable. In this embodiment as well, the inner ear housing is thereby dimensioned so that it is insertable into an opening between a middle ear and an inner ear of a person, such that an inner ear area projects at least partially into the inner ear so that the at least one sound transmission window is located in the inner ear. That which was stated above regarding the other embodiment of the invention analogously applies with respect to the inner ear housing, the sound transducer, and the sound transmission window.

The electrode carrier in the embodiment of the invention described here is arranged so that it extends from the inner ear area in the direction away from the sound transducer. If the sound transducer is thus arranged on one side of the inner ear area, then the electrode carrier extends on an opposite side of the inner ear area from this and away from the sound transducer.

In this embodiment of the invention as well, the electroacoustic transducer may advantageously have a middle ear component, which is arranged on a side of the sound transducer opposite the inner ear area. The arrangement may thus be analogous to how the invention is described in the preceding embodiment.

Advantageous refinements of all embodiments of the invention will subsequently be described.

It is advantageous that the inner ear housing and/or the inner ear area is sealed against penetration by fluid into the into the inner ear area. In this way, the inner ear area may be inserted into the cochlea, without fluid penetrating into the inner ear area.

In one advantageous embodiment, the inner ear housing may have a circular or circular arc shaped cross section about a longitudinal axis of the housing. The longitudinal axis of the inner ear housing is thereby preferably an axis which connects the sound transducer to a side of the inner ear housing opposite the sound transducer. This longitudinal axis is particularly preferably parallel to the longitudinal axis of the sound transducer. However, that axis may be considered to be a longitudinal axis, about which the inner ear housing is shaped circularly or in a circular arc, so that this longitudinal axis forms a center axis of the inner ear housing. The electroacoustic transducer may be implanted, for example, via a mastoidectomy. In this surgical technique, the transducer is often implanted through an opening which is spanned by the facial nerve and the chorda tympani nerve. These two nerves form a triangular structure, together with the osseous wall of the middle ear. Therefore, the inner ear housing may also be configured with a triangular cross section or periphery for such an implantation.

The inner ear housing may have one or more side walls. These may be those walls which are adjacent to the sound transducer or face it. The inner ear housing may also have an end wall, which is a wall opposite the sound transducer with respect to the inner ear area.

In the area of the at least one sound transmission window, the inner ear housing preferably has a lower mechanical impedance than in the area outside of the at least one sound transmission window. In particular, the sound transmission window may be provided as an area of the wall of the inner ear housing in which the inner ear housing has a lower mechanical impedance. An opening surface of the sound transmission window preferably forms a mutual surface with a wall of the inner ear housing, such that the sound transmission window thus preferably forms a partial area of a wall of the inner ear housing, or a recess therein, which is not the entire corresponding wall.

In one advantageous embodiment, the inner ear housing may taper along a longitudinal axis of the inner ear area in the direction away from the sound transducer. The longitudinal axis of the inner ear area may coincide the longitudinal axis of the inner ear housing. In general, an axis may be considered as the longitudinal axis of the inner ear area which extends from the sound transducer to a side of the inner ear area opposite the sound transducer. The longitudinal axis of the inner ear area may preferably be an axis of symmetry of the inner ear area and/or of the inner ear housing, also, in some embodiments, also of the electrode carrier which may connect to the inner ear housing, and/or of the outer shaft which may connect to the middle ear component.

That the inner ear area tapers in the direction away from the sound transducer may mean that a diameter of the inner ear area and/or an edge length of the inner ear area and/or a diagonal of the inner ear area decreases along the longitudinal axis in a direction away from the sound transducer.

In one advantageous embodiment of the invention, the inner ear housing may have a section along a longitudinal axis of the inner ear area in which the diameter or an extension of the inner ear housing in a direction perpendicular to said longitudinal axis is greater than the diameter of the inner ear housing at the opening between the middle ear and the inner ear of the respective person when the electroacoustic transducer is inserted as intended into the opening. As a result, the inner ear housing is insertable as far into the relevant opening between the middle ear and the inner ear until the dimensions of the inner ear housing in the direction perpendicular to the longitudinal axis in at least one dimension are greater than the dimensions of the corresponding opening between the middle ear and inner ear in the same direction. This section with the larger diameter may also advantageously be part of the tapering shape of the inner ear housing. In this way, a point of impact may be created, up to which the electroacoustic transducer is insertable into the corresponding opening between the middle ear and the inner ear, which simplifies the implantation. To orient the transducer about its longitudinal axis, one or more markings may be applied on the outer side of the electroacoustic transducer which indicate the orientation about the longitudinal axis.

The sound transducer is preferably arranged so that it extends in a plane which is parallel to or tilted at an angle less than 45° to a plane which is perpendicular to the longitudinal axis of the inner ear housing. The plane may also be described as a plane which is tilted at an angle of less than 45° and is preferably parallel to a plane which is spanned by the normal vectors of the longitudinal axis of the inner ear housing. This arrangement of the sound transducer is particularly advantageous if the sound transducer is itself configured as flat, as will be subsequently described. Reference is made to the fact that the sound transducer may also be arranged tilted at larger angles and in particular its surface may also be parallel to the longitudinal axis of the inner ear area or the inner ear housing.

In one advantageous embodiment of the invention, the sound transducer may have a membrane structure which has at least one carrier layer and at least one piezoelectric layer having at least one piezoelectric material arranged on the carrier layer. The at least one carrier layer and the at least one piezoelectric layer thus form a layer system in which the carrier layer and the piezoelectric layer are arranged parallel on top of one another. In this embodiment, vibrations of the membrane structure may be generated by applying a voltage to the piezoelectric layer, in particular an alternating voltage. This utilizes the fact that the piezoelectric layer deforms when the voltage is applied, wherein the direction of the deformation depends on the sign of the applied voltage. A membrane structure may herein be understood as a structure which extends substantially flat, which has a significantly higher extension in two dimensions than in the dimension perpendicular to the two dimensions. The two dimensions, in which the membrane structure primarily extends, thereby span a membrane surface and the surface of the sound transducer.

The membrane structure of the sound transducer may be divided by at least one cut line in its flat extension into at least one, two, or more segments. Dividing the membrane surface means that the entire membrane, thus both the carrier layer and also the piezoelectric layers, and, if necessary, electrode layers, are divided by mutual cut lines, such that the membrane is mechanically decoupled at the cut line(s), which means that two areas of the membrane structure, separated by a cut line, are movable independently of one another. The division or segmentation of the membrane surface thus means a corresponding segmentation of the carrier layer and corresponding segmentation of the piezoelectric layer and, if necessary, electrode layers.

The segmentation enables a high amplitude of a vibration at very small installation size without the force becoming too low due to these measures.

Sound vibrations are understood in the meaning of the application to be vibrations with frequencies which are perceivable by human hearing, are or lie in a range below or above human perception, i.e., vibrations between approximately 2 Hz and 20,000 up to 30,000 Hz. The sound vibrations are additionally suited for exciting sound waves in a medium, in particular air or perilymph.

The membrane structure advantageously has at least one carrier layer and at least one piezoelectric layer, which has at least one piezoelectric material, arranged on the carrier layer. The carrier layer and the piezoelectric layer then form a bimorph structure and are therefore advantageously arranged and designed so that the membrane structure is oscillatable by applying a voltage, in particular an alternating voltage, to the piezoelectric layer, and/or voltages in the piezoelectric layer generated by vibrations of the membrane are detectable. The carrier layer and the piezoelectric layer may hereby be arranged with parallel layers planes on top of one another or on one another and should be directly or indirectly connected to one another. The aforementioned cut lines preferably sever all layers of the membrane structure.

In order to guarantee good audiological quality, the membrane structure is advantageously designed so that it enables a maximum deflection from 1 to 5 μm, preferably of 5 μm.

For this purpose, e.g., at a frequency v of 4 kHz, an acoustic flow impedance ZF of the round window of 32 GΩ and an area A of the membrane of the round window of approximately 2 $mm^2$, a driving force of 2 πv $Z_F A^2 x$=1.6 10-2 N is necessary. The average energy corresponds to half of the product of the maximum force and maximum deflection, thus, in this example, 4.10-8 J in order to obtain the performance. Converted to an installation space of, e.g., 2 $mm^3$, an energy density of 20 $J/m^3$ is required in this example.

The segments may be configured so that the impedance is optimal, in particular with respect to their length.

It is particularly preferred that the membrane structure is carried out in thin layer technology. Thin layers are advantageous, as high fields are required to generate high energy densities; whereas the applied voltages are to be as low as possible because of the biological surroundings. The necessary energy densities are achievable in a thin layer membrane.

In particular, the piezoelectric layers according to the invention may thereby be produced in thin layer technology. To produce a piezoelectric layer of the membrane structure, piezoelectric material is applied in the thickness of the piezoelectric layer. The application may be carried out using deposition techniques, like physical vapor deposition, chemical vapor deposition, and others. By producing the piezoelectric layers through deposition of piezoelectric material in the desired thickness, significantly thinner piezoelectric layers may be realized than according to the prior art, in which completely grown piezoelectric crystals were abraded to the thickness of the piezoelectric layer.

The piezoelectric layers preferably have a thickness of ≤20 μm, preferably ≤10 μm, particularly preferably ≤5 μm and/or ≥0.2 μm, preferably —1 μm, preferably ≥1.5 μm, particularly preferably=2 μm. The electrode layers advantageously have a thickness of ≥0.5 μm, advantageously ≤0.2 μm, particularly preferably ≤0.1 μm and/or ≥0.02 μm, advantageously 0.05 μm, and particularly preferably ≥0.08 μm.

Thin layers of the sound transducer—both the silicon beam structure and also the piezoelectric layer(s)—ensure that only a small mass is set into movement by the deflection of the beams. The resonance frequency of the vibration system for the described actuator variants is located in the upper range of the frequency bandwidth of human hearing. Thus, a uniform excitation of the round window across the entire human frequency range is possible.

The generation of the mechanical vibrations of the sound transducer according to the invention is thereby based on the principle of elastic deformation of a bending beam, wherein the membrane or segments of the membrane may be considered to be bending beams. The piezoelectric layer (piezo layer) is able to be shortened or lengthened by applying the voltage and the electrical field generated thereby. Mechanical stresses are hereby generated in the material composite made of the carrier layer and piezoelectric layer, which lead to an upward bending of the beams or the membrane structure in a shortening piezoelectric layer and to a corresponding downward movement in the case of a lengthening piezoelectric layer. Whether the piezoelectric layer lengthens or shortens depends on the polarization direction of the piezoelectric layer and the direction of the applied voltage or the applied electrical field.

In the case of a single-layer sound transducer, the described carrier layer may carry a single layer of piezoelectric material. In addition, the electrodes form further components of the layer structure. A bottom electrode may thereby be applied directly or via a barrier layer onto the silicon substrate, whereas in contrast, a top electrode may be located on top of the piezoelectric layer.

The polarization direction of the piezoelectric material is preferably perpendicular to the surface of the silicon structure. If an electric voltage is now applied between the top and bottom electrodes and an electrical field forms, then the piezoelectric material shortens or lengthens (depending on the sign of the voltage) in the beam longitudinal direction due to the transversal piezoelectric effect, mechanical stresses are generated in the layer composite, and the beam structure undergoes a bending.

It is preferred if the membrane structure has a circular or oval periphery. In particular, it is favorable if the periphery of the membrane structure hereby corresponds to the periphery of the round or oval window of an ear, such that the peripheral line of the membrane structure runs parallel to the periphery of the round or oval window when the sound transducer is implanted. It may also be advantageous if the membrane structure has such a periphery that facilitates the guiding of the membrane structure through the posterior tympanotomy. In a first approximation, this may correspond to an oval periphery; however, it may also be an approximately triangular periphery. An n-cornered periphery of the membrane structure, where n is preferably ≥8, is also possible.

In particular in the case of a circular periphery, however also for other shapes of the membrane structure, it is further preferred if the cut lines, which divide the membrane surface into segments, run radially from an edge of the membrane structure in the direction of a center point of the membrane. The cut lines do not have to start directly at the edge and do not have to reach the center point; it is also sufficient if the cut lines run from the vicinity of the edge up to the vicinity of the center point. If, however, the cut lines do not reach the center point, then a free area, in which the cut lines end, should be present in the center point, such that the mechanical decoupling of the segments is guaranteed at that end facing the center point.

The segments may be hereby configured so that they are pie wedge shaped; thus, having two edges as side edges running in an angle to one another and an outer edge which runs on the periphery of the membrane structure parallel to this periphery. At the other end of the side edges, opposite the outer edge, the segments may run together into a point or be cut so that a free area results around the center point. At the edge, the segments may then be permanently arranged on the edge of the membrane structure and be independent of one another at the side edges and, if necessary, at that edge facing the center point, such that they may vibrate freely about the outer edge. The largest deflection will hereby normally occur at that edge of the segment facing the center point. The number of segments is preferably ≥8.

The cut lines may run radially straight, such that the segments have straight radial edges.

However, it is also possible that the radially-extending cut lines extend in a curve, such that segments result without straight, radially-extending edges. In particular, segments may thus be formed which extend in the radial direction in an arch shape, wave shape, or along a zigzag line. Numerous other geometries are also conceivable.

In one alternative embodiment of the invention, the membrane structure may be structured by at least one spiral-shaped cut line. The at least one cut line thereby runs so that at least one spiral-shaped segment results, which preferably winds about a center point of the membrane structure. It is also possible to provide multiple cut lines, which divide the membrane structure so that two or more spiral-shaped segments result, which advantageously respectively wind about the center point of the membrane structure and particularly preferably run into one another.

In order to oscillate the membrane structure and/or in order to tap a voltage at the piezoelectric layer, at least one first and at least one second electrode layer are arranged on the on the membrane structure, wherein the at least one piezoelectric layer is arranged between the first and the second electrode layer. The electrode layers hereby preferably cover the piezoelectric layer and are arranged with parallel layer planes on or on top of the piezoelectric layer. The first or second electrode layer is preferably arranged between the carrier layer and the piezoelectric layer, such that the piezoelectric layer is arranged over one of the electrode layers on top of the carrier layer. The piezoelectric layer and the electrode layers particularly preferably completely cover one another.

The use of segment structures enables a higher deflection, in contrast to an unstructured membrane, as the beam elements may freely deform where they are separated by the cut lines, e.g., in the center of the disk, and thus undergo a constant bending in only one direction. In contrast, the deformation of a coherent membrane is characterized by a change of direction of the curvature, which leads to smaller deflections.

In one preferred embodiment, the membrane structure has a plurality of piezoelectric layers arranged with parallel surfaces on top of one another, wherein an electrode layer is arranged between each two adjacent piezoelectric layers. An electrode layer and a piezoelectric layer are thus respectively arranged alternating on the carrier layer. Electrode layers and piezoelectric layers may be arranged directly on top of one another, connected to one another, or arranged on top of one another via one or more intermediate layers. Vibrations with a particularly large force or power may be generated and vibrations may be detected particularly precisely with this embodiment.

Electrodes with different electrical potential alternate with piezoelectric layers in the layer structure in this transducer modification. The silicon structure is initially followed by a bottom electrode, followed by a first piezoelectric layer, an electrode with opposite potential, a second piezoelectric layer, an electrode with the potential of the bottom electrode, etc.

The polarization direction of the individual piezoelectric layers may be perpendicular to the surface of the membrane structure, as is the case in the single-layer transducer; however, it faces in the opposite direction for alternating piezoelectric layers. The electrical field building up between the electrodes of opposite potentials and the polarization direction alternating for the individual piezoelectric layers ensures a mutual change in length of the entire layer structure, which in turn causes the silicon structure to bend.

The electrode layers are advantageously configured or contacted so that a charge with a different polarity may be applied to each two adjacent electrode layers. By this means, an electrical field may be generated in the piezoelectric layers which extends in each case from one electrode layer to the adjacent electrode layer. In this way, the piezoelectric layers may be penetrated particularly uniformly with electrical fields. In the case of a vibration detection, different signs of a voltage arising at the piezoelectric layer may preferably be tapped in each case by adjacent electrode layers.

In another advantageous embodiment of the present invention, at least two strip-shaped, thus elongated electrodes, which form an electrode pair, are arranged on the surface of the at least one piezoelectric layer or on the surface of the carrier layer so that they extend parallel to the corresponding surface and preferably also extend parallel to one another. A charge with a different polarity is able to be respectively applied to the two electrodes of an electrode pair such that an electrical field forms between the electrodes of an electrode pair and penetrates the piezoelectric layer at least in sections. If multiple electrode pairs are provided, an electrode field may also form between electrodes of different polarities of adjacent electrode pairs and penetrate the piezoelectric layer. In the case of vibration detection, an electrical voltage is able to be tapped or detected by the electrode pair.

The strip conductor structures of the strip-shaped electrodes may preferably have a rectangular cross section.

It is particularly advantageous if a plurality of electrode pairs, each comprising two electrodes to which different polarities are able to be applied, are arranged so that the electrodes of the plurality of electrode pairs extend parallel to one another. The electrode pairs should thereby be additionally arranged so that charges of different polarity are able to be applied to two adjacently-extending electrodes. In this way, an electrical field, penetrating the piezoelectric layer, forms between each two adjacent electrodes. In the case that, as described here, a plurality of electrode pairs is provided, then a plurality of electrodes is present on one surface of the piezoelectric layer or of the carrier layer and may extend parallel to one another and may be arranged adjacent to one another with alternating polarity.

The polarity of the piezoelectric material is not distributed homogeneously across the entire piezoelectric layer in the case; instead, the polarization direction extends from the negative to the positive electrode forming line-shaped fields.

During operation of the transducer, when an alternating electrical potential is applied to the comb-shaped electrodes, then an electrical field forms along the polarization direction of the piezoelectric material, along which field the piezoelectric material extends or shortens. By this means, the entire piezoelectric layer lengthens or shortens in the beam longitudinal direction, which leads to an upward bending or downward bending of the silicon structure.

It is particularly advantageous if the electrodes additionally extend parallel to the edge of the membrane structure in this case. If the membrane structure is circular, then the electrodes preferably form concentric circles about the center point of the membrane structure. Correspondingly, the electrodes are also preferably configured to be oval in the case of an oval membrane structure. The electrodes may each extend along the entire periphery parallel to the periphery of the membrane structure, or only on a part of the periphery, such that they have, for example, the shape of circular arc sections.

Strip-shaped electrodes may be particularly advantageously contacted via mutual conductors, wherein a plurality of electrodes may be contacted by one mutual conductor. Thus, a plurality of electrodes of one polarity may be connected to at least one first conductor and electrodes of the other polarity may be connected to at least one second conductor.

In order that the electrodes of different polarities are arranged alternatingly, the electrodes of different polarities assigned to the different conductors may mesh into one another in a comb shape. The mutual conductors may hereby cut the electrodes of their corresponding polarity and extend, e.g., preferably radially in the case of circular electrodes.

In the case of a strip-shaped embodiment of the electrodes, the membrane structure may also be designed as multilayered. It is again possible that multiple piezoelectric layers are arranged on top of one another, wherein strip-shaped electrodes may then extend between two respectively adjacent piezoelectric layers. The arrangement of electrodes hereby corresponds to the arrangement on the surface of a piezoelectric layer described above. However, it is also possible that the membrane structure has at least one piezoelectric layer which is penetrated by strip-shaped electrodes or electrode pairs in one or more planes.

In this case, the electrodes of the electrode pairs extend in the interior of the corresponding piezoelectric layer. The different possibilities for the arrangement also correspond here to that of the abovementioned arrangement on the surface of the piezoelectric layer.

This variant of the sound transducer has a thicker piezoelectric layer, which, in contrast to the previous solution, may be penetrated by multiple layers of comb-shaped electrodes. The polarization in the piezoelectric material runs again from the negative to the positive strip conductor electrode forming line-shaped fields. Upon applying a voltage, an electrical field forms along the polarization direction which leads to an extension or shortening of the piezoelectric material along the field lines and to a downward bending or upward bending of the beam structure.

In the case of spiral-shaped segments, strip-shaped electrodes may be arranged along the longitudinal direction of the segments. One electrode pair is preferably sufficient in this case.

Since the sound transducer is used in a biological environment, it is advantageous if the voltage, which is applied to the electrodes, is less than 3 volts, preferably less than 2 volts, particularly preferably less than 1.3 volts. Alternatively or additionally, it is also possible to encapsulate the electrodes to be liquid tight and/or electrically insulated, such that they do not come into contact with an optional fluid surrounding the sound transducer.

Since the piezoelectric effect in the relevant area is proportional to the strength of the electrical field which penetrates the material, high fields (the electrical field is calculated in the homogeneous case as the quotient of the applied voltage and the distance of the electrodes) may be generated by using very thin piezoelectric layers at very small distances of the electrodes, so that the piezoelectric effect is sufficient to achieve the necessary vibration deflections and forces necessary to excite the round window.

The carrier layer may have or comprise silicon. Suitable piezoelectric materials include, among others, PbZrxTi1-xO3, where preferably $0.45<x<0.59$, particularly preferably with dopants of, for example, La, Mg, Nb, Ta, Sr and the like, preferably at concentrations between 0.1 and 10%.

Additional solid solutions comprising PbTiO3, for example Pb(Mg⅓, Nb⅔)O3, Pb(Sn⅓Nb⅔)O3 are also suitable. Possible materials are also lead-free materials which contain KNbO3, NaNbO3, dopants with Li, Ta, etc., bi-containing piezoelectric layers, aurivilius phases comprising Ti, Ta, Nb, additionally also perovskite phases, like BiFe3. Conventional thin layer materials, like AlN and ZnO, are also possible.

Silicon as a carrier material for the piezoelectric layers enables the production of the disk-shaped structure and the pie wedge shaped bending beams using the structuring techniques of microsystem technology. Known and proven coating and etching methods may be used for producing beams, electrodes and the piezoelectric layer, e.g., sol-gel techniques, sputtering methods, chemical etching, ion etching, etc. Furthermore, the methods of microsystem technology allow parallelization in the manufacturing process: a plurality of sound transducers may be produced from one silicon wafer in one pass through a manufacturing process. This enables cost efficient production.

The at least one piezoelectric layer advantageously has a thickness of ≤20 μm, advantageously ≤10 μm, particularly preferably 5 μm and/or ≥0.2 μm, advantageously ≥1 μm, preferably ≥1.5 μm, particularly preferably=2 μm. The electrode layers each advantageously have a thickness of ≤0.5 μm, advantageously ≤0.2 μm, particularly preferably ≤0.1 μm and/or 0.02 μm, advantageously ≥0.05 μm, particularly preferably ≥0.08 μm. A diameter of the membrane structure is advantageously ≤4 mm, preferably ≤3 mm, particularly preferably ≤2 mm and/or ≥0.2 mm, advantageously ≥0.5 mm, preferably ≥1 mm, particularly preferably=1.5 mm. A layer thickness of 0.7 μm has also proven particularly favorable.

According to the invention, the sound transducer may also have a plurality of the membrane structures described above. These membrane structures are thereby identically structured and arranged above one another and parallel to one another so that identical segments of the structure or the cut lines of the membrane structures lie over one another. Identical segments may then be coupled to one another so that a deflection and/or application of force of one of the segments transmits to the adjacent segments. The membrane structures may thereby be arranged above one another so that, upon applying a voltage of a defined polarity to the sound transducer, all segments are deflected in the same direction. The membrane structures are hereby identically oriented. In this case, a total force may be realized which is higher than that of a single membrane structure. It is also possible to arrange the membrane structures on top of one another so that adjacent membrane structures are respectively oriented in opposite directions, such that, upon applying a voltage of a defined polarity, adjacent membrane structures respectively deflect in different directions. In this case, a total deflection may be realized which is greater than that of a single membrane structure.

The membrane structure may preferably be divided in the surface of the membrane structure by at least one cut line severing all layers of the membrane structure into at least one, two, or more segments, such that the membrane structure is mechanically decoupled at the cut lines. The membrane structure being mechanically decoupled at the cut lines thereby means that, a movement of the membrane structure on one side of the cut line does not cause any, or only a very small movement of the membrane structure on the opposite side of the cut line, which would be caused in the case that a force acts across the cut line. If the membrane structure is divided into two or more segments, then these may be formed, for example, by radially extending cut lines. In this case, for example, the membrane structure may itself have a circular periphery in the plane of the membrane structure, and the cut lines extend radially to this center point. All cut lines are thereby preferably mechanically decoupled in the center point.

If the membrane structure has only one cut line, then this may particularly advantageously extend in a spiral shape. The membrane structure in this case may also advantageously have a circular periphery.

In one advantageous embodiment of the invention, the at least one sound transmission window may be provided in a side wall of the inner ear housing surrounding a longitudinal axis of the inner ear area and/or may be provided in an end wall delimiting the inner ear area on a side facing away from the sound transducer in the direction of the longitudinal axis of the inner ear area. Sound transmission windows arranged in the side wall are primarily advantageous if an elongated electrode carrier is provided, as the vibration transmission is not impeded by the electrode carrier.

One side wall surrounding the longitudinal axis of the inner ear area may advantageously have the shape of a partial surface of a conical surface. This has a circular periphery perpendicular to the longitudinal axis and tapers in the direction of the longitudinal axis. If a sound transmission window is arranged in this side wall then it preferably surrounds the longitudinal axis of the inner ear area only on a part of the total periphery and/or extends only on one part of the total extension in the direction of the longitudinal axis.

In one advantageous embodiment, the inner ear housing may have, on the one side, one section in which the inner ear housing tapers along its longitudinal axis and, on the other side, a cylindrical section adjacent thereto, whose cylindrical axis is coaxial to the longitudinal axis of the inner ear area. The tapering section is preferably adjacent to the sound transducer at its widest end and to the cylindrical section at its narrowest end. The cross section, both in the tapering section and also in the cylindrical section, is preferably circular or circular arc shaped in planes perpendicular to the longitudinal axis. In this embodiment, it is particularly preferred if the at least one sound transmission window is arranged in the cylindrical section. A diameter of the cylindrical section is preferably smaller than an extension of the opening between the middle ear and inner ear of the relevant person in the direction of the smallest extension of this opening. In this way, the cylindrical section may be completely inserted into the inner ear until the tapering section contacts an edge of the corresponding opening between the middle ear and inner ear.

The at least one sound transmission window may preferably have a flexible and/or biodegradable membrane which covers the surface of the sound transmission window. In this way, the sound transmission window enables a passage of vibrations from the inner ear area into the perilymph of the cochlea. If the at least one sound transmission window has such a flexible and/or biodegradable membrane, which covers the surface of the sound transmission window, then in one advantageous embodiment, this membrane may completely or partially cover the entire surface of the electroacoustic transducer and/or the electrode carrier. In particular, the membrane may then also be present on an outer side of the inner ear housing and/or the electrode carrier in sections, in which the sound transmission window is not present and are thus formed by the actual wall of the inner ear housing or the outer surface of the electrode carrier. A biodegradable membrane is a membrane which dissolves in the ear over time. By using such a membrane, it may be guaranteed that, during the implantation and during the subsequent healing, the sound transmission window is closed so that cochlear fluid only enters into the inner ear housing after successful implantation and healing. In this way, an embodiment of the invention may be realized in which the cochlear fluid contacts the sound transducer without causing complications during healing.

The inner ear area may advantageously be at least partially filled with a vibration transmission material, so that the vibration transmission material contacts the sound transducer and the at least one sound transmission window. In the simplest case, the inner ear area may be completely filed with the vibration transmission material, such that the vibration transmission material is present on both the sound transducer and also on the sound transmission window.

The vibration transmission material may be a solid, whose modulus of elasticity is preferably lower than the modulus of elasticity of the inner ear housing. It is particularly preferred that the modulus of elasticity of the solid is then less than or equal to 10%, particularly preferably less than or equal to 1% of the modulus of elasticity of the inner ear housing. In particular, the solid may advantageously have or comprise silicone.

The vibration transmission material may advantageously also be a fluid, which has a modulus of compression greater than or equal to 0.1 GPa, preferably greater than or equal to 1 GPa, particularly preferably greater than or equal to 2 GPa. In particular, the vibration transmission material as a fluid may have or comprise water, silicone oil, and/or white mineral oil.

If the described electrode carrier is provided, then advantageously at least one part of a surface of the electrode carrier may have or comprise the vibration transmission material, with which the inner ear housing is filled. In this way, a materially integral transition may be produced between the interior of the inner ear housing, thus the inner ear area, and the surface of the entire structure. The electrodes of the electrode carrier are thereby preferably exposed.

Regardless of whether an electrode carrier is provided or not, the electroacoustic transducer may also itself be completely or partially covered by the vibration transmission material on its outer surface. In this way, a materially integral connection results for transmitting vibrations between the inner ear area and the outer surface of the electroacoustic transducer.

In one preferred embodiment of the invention, the middle ear component may have a medium which contacts the sound transducer. The medium may thereby advantageously be a solid with a modulus of elasticity that is lower than the modulus of elasticity of the inner ear housing, wherein the modulus of elasticity of the solid is preferably less than or equal to 10%, particularly preferably less than or equal to 1% of the modulus of elasticity of the inner ear housing. In particular, this solid may advantageously comprise or consist of silicone.

The middle ear component may preferably have a middle ear housing enclosing a middle ear area, wherein the middle ear area is delimited on one side by the at least one sound transducer. In this embodiment, the middle ear housing thus surrounds the middle ear area. The middle ear housing may thereby have one or more walls which enclose the middle ear area.

In one advantageous embodiment, the middle ear area may then be filled with a solid, liquid, or gaseous medium, wherein the medium may contact the sound transducer and may affect a lower impedance of the middle ear area than a potentially present vibration transmission material, with which the inner ear area may be at least partially filled. Due to the selection of the material for the middle ear area, it is achieved that the movement of the sound transducer is hampered at little as possible. At the same time, the middle ear component prevents overgrowing of the sound transducer. The compressibility of the medium is not decisive here. A compressible medium may be advantageous, as a closed volume may thus be realized in the middle ear component.

In the case of one advantageous embodiment, the medium may advantageously be a fluid, which has a modulus of compression greater than or equal to 0.1 GPa, preferably greater than or equal to 1 GPa, particularly preferably greater than or equal to 2 GPa. In particular, the fluid may advantageously have or comprise water, silicone oil, and/or white mineral oil.

The middle ear housing may advantageously have at least one window which is incorporated in a wall of the middle ear housing. The window may be advantageously arranged in a side wall, which is a wall that is adjacent to or faces the sound transducer; however, it is also possible that such a window is additionally or alternatively arranged in an end wall, which is a wall that is opposite the sound transducer.

In one advantageous embodiment of the invention, the middle ear housing may be formed from at least partially from one, two, or more wires and a sheath surrounding the wires, wherein the wires and the sheath are mechanically connected to one another. These wires may contact the sound transducer or the at least one electrode of the electrode carrier. Ribbon cables are particularly suited as these wires, as these guarantee a particularly high stability of the housing.

It is also possible to form the middle ear area from a solid, as described above, wherein this solid may be stabilized by one or more wires.

The middle ear housing may advantageously taper along a longitudinal axis of the middle ear area in the direction away from the sound transducer. The middle ear housing may advantageously have a circular cross section. In one particularly preferred embodiment, the middle ear housing may have the form of a partial surface of a cone. If the housing tapers away from the sound transducer, then it has its largest extension at the sound transducer, thus its largest diameter or its largest diagonal, and its smallest extension on the side facing away from the sound transducer. The inner ear housing may preferably have a smaller minimum diameter in the direction perpendicular to the longitudinal axis of the inner ear housing than the middle ear component. The tapering of the middle ear component may be advantageous, since the sound transducer may then have a larger diameter than a rearward shaft of the electrode carrier in the direction of the middle ear.

In one preferred embodiment of the invention, the inner ear housing and/or the middle ear area and/or the middle ear housing may have at least one channel on its outer side, through which the at least one wire runs in the direction of the longitudinal axis of the respective housing. This wire may be electrically contacted with the at least one electrode of the electrode carrier. In this way, it is possible to contact and apply an electrical signal to the electrodes of the electrode carrier or also the electrodes of the sound transducer. In one advantageous embodiment, two channels of this type may be provided, through which one wire respectively runs. In this way, different polarizations of the contacting of the sound transducer may be enabled, or a redundancy for contacting the at least one electrode of the electrode carrier may be enabled if one of the wires fails.

Wires, for example, bond wires, welded wires, or flexible conductor strips, may be used for the electrical contacting and which may likewise be embedded in a silicone layer or the sleeve and may be guided to the implant electronics.

The inner ear housing and/or the middle ear housing and/or at least parts of the electrode carrier may advantageously be completely or partially coated on its or their outer side(s) with a sleeve material or surrounded by the same, wherein, however, the electrodes of the electrode carrier preferably remain exposed. In this way, the electroacoustic transducer may be designed to be biocompatible.

The wires for contacting the electrodes of the cochlear implant, thus the electrode carrier, may advantageously be guided past the sound transducer and the middle ear area and the inner ear area if necessary. It is possible, as described, to integrate or embed the wires into the sleeve material, if this is present. It is also possible to overmold the sleeve and the sound transducer with silicone in order to embed the electrode wires therein.

In addition, the sleeve material may advantageously also form the surface of the electrode carrier. The sleeve material may advantageously have or comprise a silicone. It is preferably applied so that it produces or reinforces a mechanical connection between the inner ear housing and the electrode carrier.

In one advantageous embodiment of the invention, the sleeve material may have at least one segment in the area of the at least one sound transmission window in the inner ear housing and/or in the middle ear housing, said sound transmission window having or comprising a vibration transmission material in each case. The vibration transmission material is thereby preferably a solid with a modulus of elasticity that is lower than the modulus of elasticity of the inner ear housing, wherein the modulus of elasticity of the solid is particularly preferably less than or equal to 10%, preferably less than or equal to 1% of the modulus of elasticity of the inner ear housing. In particular, the solid may in particular have or comprise a silicone. In this way, a window in the inner ear housing and/or in the middle ear housing may be sealed by the corresponding segment.

It is particularly advantageous if the surface of the at least one segment is flush with the surface of the sleeve material or connects to the surface of the inner ear housing or of the middle ear housing. In addition, it is particularly advantageous if the at least one segment comprises or consists of a vibration transmission material, which enables a substantially loss-free transmission of sound vibrations from the inner ear area to the outside or vice versa, as the sleeve material or the material of the corresponding housing enables at the same geometry.

The inner ear housing and/or the middle ear housing may advantageously be produced from a plastic material, polyimide, PEEK, polyamide, silicone, epoxy resin, PET, metal, metal alloy, gold, platinum, titanium, titanium alloy, aluminum, ceramic, glass, quartz glass, zirconium oxide, and/or aluminum oxide or a combination of these materials.

The electroacoustic transducer is preferably dimensioned as follows. A minimum diameter of the inner ear housing may advantageously be less than or equal to 3 mm, particularly preferably less than or equal to 1 mm and/or greater than or equal to 0.3 mm, preferably greater than or equal to 0.6 mm. A length of the inner ear housing in the direction of the longitudinal axis may advantageously be less than or equal to 3 mm, preferably less than or equal to 2 mm and/or greater than or equal to 1 mm, preferably 1.85 mm. A diameter of the sound transducer may advantageously be less than or equal to 5 mm, preferably less than or equal to 3 mm and/or greater than or equal to 0.8 mm, preferably 1.3 mm. A length of the middle ear housing may advantageously be less than or equal to 20 mm, preferably less than or equal to 15 mm and/or greater than or equal to 3 mm, preferably 10 mm.

The sound transducer is preferably an actuator. The opening between the middle ear and the inner ear of the person may be a round window or an oval window of an ear of the person or an opening created between the middle ear and the inner ear of the person, which is introduced, for example, by a doctor.

The sound transducer may advantageously be equipped to generate an electrical voltage from an acoustic signal. A voltage, which is able to be applied to at least one of the electrodes, is thereby controlled by the voltage generated by the sound transducer. In this way, an acoustic signal may be transmittable to the electrodes.

It is possible to provide more than one sound transducer. In this way, a maximum generatable sound pressure may be increased. If the sound transducers are designed to be flat, as described above, in particular as membrane structures, then a plurality of these sound transducers may be arranged over one another with coaxial center axes.

In one advantageous embodiment, the inner ear housing and/or the middle ear housing may be reverberative. An outer surface of the middle ear housing and/or the inner ear housing may preferably have or comprise at least partially, preferably at least 5% of a solid material.

In one advantageous embodiment, one or more markings may be provided on the middle ear housing, on the inner ear housing, and/or on the sound transducer, which enable the orientation of the electroacoustic transducer about its longitudinal axis to be determined. In this way, it may be ensured during inserting into the ear that the sound transmission windows are correctly oriented.

Additionally, a method according to the invention is specified for producing an electroacoustic transducer as described above. A tubular semi-finished product in the form of the inner ear housing and/or the middle ear housing is thereby shaped, which produces at least one sound transmission window. The inner ear housing and/or the middle ear housing is thereby preferably produced at least partially by means of generative methods.

If the electroacoustic transducer has a cylindrical base form with a constant diameter, then it may be produced from a tubular semi-finished product by means of laser processing. The laser may thereby cut the windows and other recesses or dividing lines into the material for reducing the flexural strength. The tubular semi-finished product may be cut to the correct dimension before or after this processing. In the case of a tapering middle ear housing and/or inner ear housing, thus corresponding housings which have a cross section that changes along their longitudinal axes, a tubular semi-finished product may initially be shaped into a tube with a defined, variable diameter. This may be realized, for example, using a semi-finished product made from shrink material. Extruded tubes made from thermoplastic material are particularly suited for this. This semi-finished product may be placed on a mandrel with the desired internal geometry and heated. It then pulls together at the periphery and conforms closely to the mandrel, such that it assumes its shape. After cooling, the semi-finished product retains the shape. Further work steps may be subsequently carried out using the laser, similar to those for a cylindrical basic structure. It is also possible to reverse the sequence, thus to carry out a laser processing first, and then a shrinking, or to carry out the work steps in parallel, thus simultaneous shrinking with the laser which is then also used for the processing.

Short pulse laser processing is advantageous in order to keep a heat input as low as possible, and thus prevent burning or deforming.

It is also possible to produce the inner ear housing or the middle ear housing by means of injection molding, also in combination with other parts of the electroacoustic transducer in multi-component injection molding. An additive production method, for example, 3D printing or three-dimensional lithographic methods, is also possible for producing the inner ear housing, the middle ear housing, and the windows.

In addition, a cochlear implant system according to the invention is specified. This has at least one microphone, at least one battery, at least one processor unit, at least one electronics for controlling stimulation pulses for the electrodes, and an electroacoustic transducer as previously described. In addition, the cochlear implant system may advantageously have an electrode carrier with at least one stimulation electrode, which may be electrically connected to the electronics for controlling stimulation pulses.

In the following, the present invention is explained in greater detail by way of example with reference to a few figures. Identical reference numbers thereby designate identical or corresponding features. The features described in the examples may also be realized independently from the specific example and may be combined between the examples.

Figure 1:
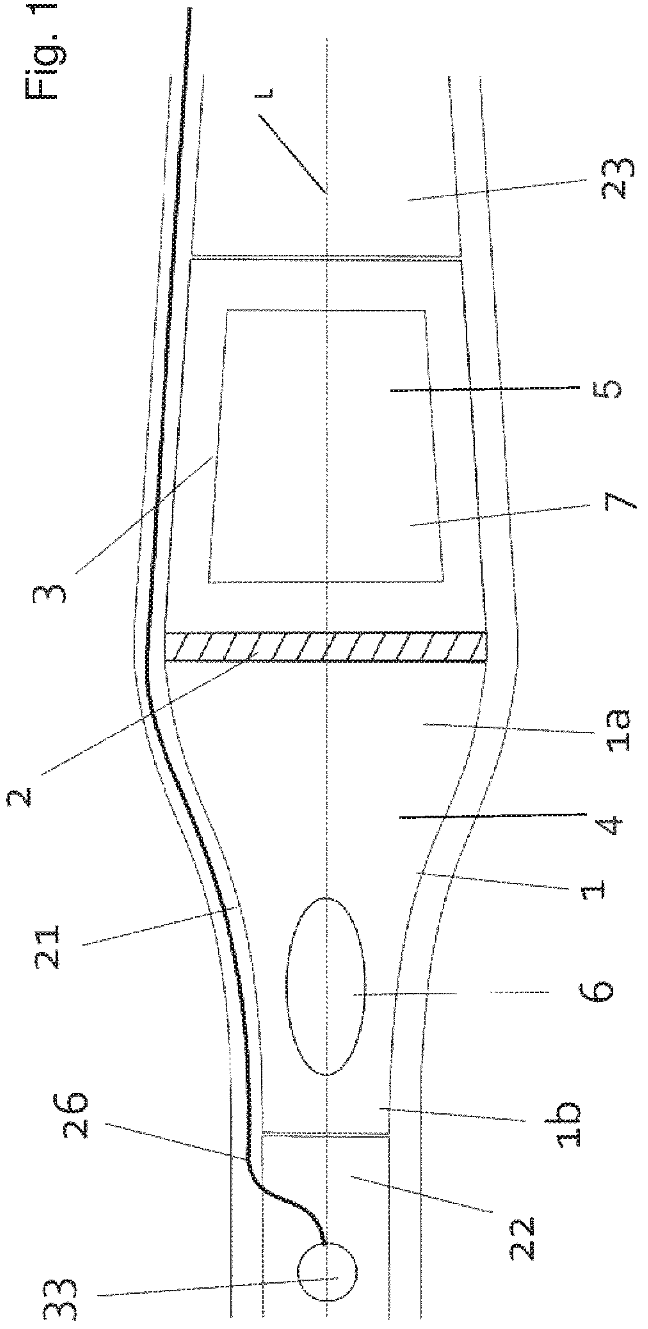
Figure 2:
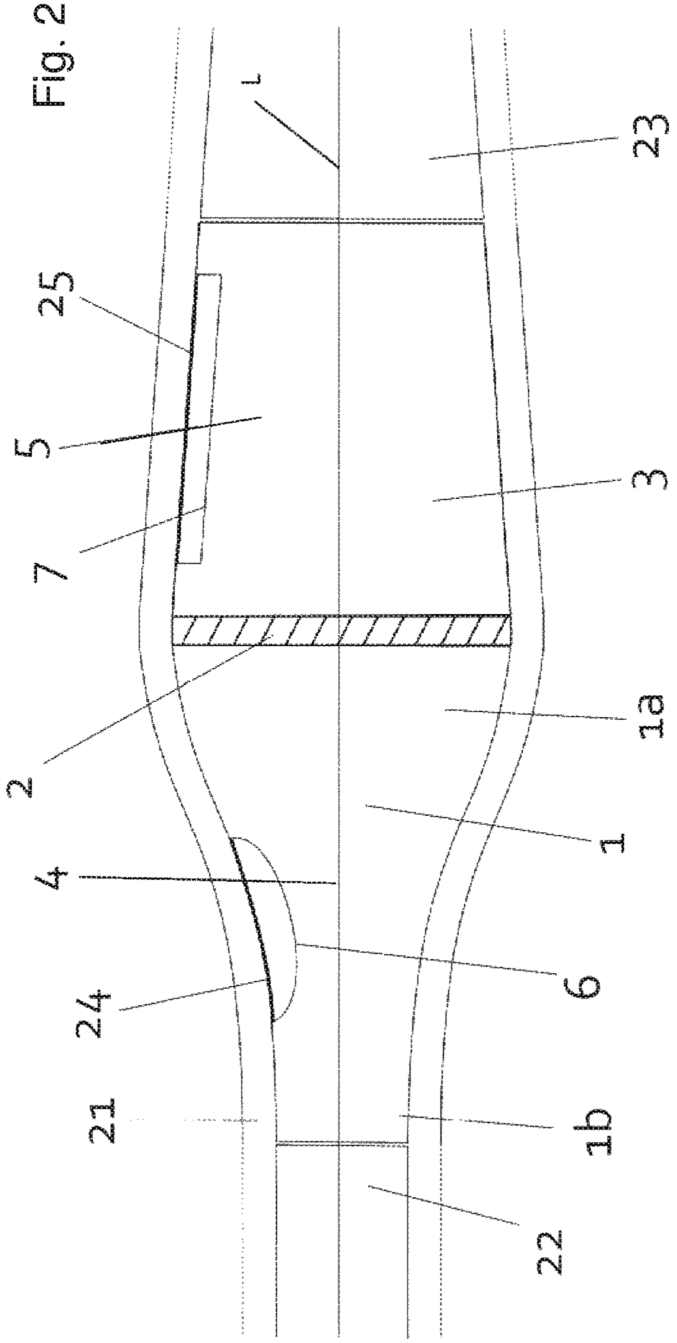
Figure 7A:
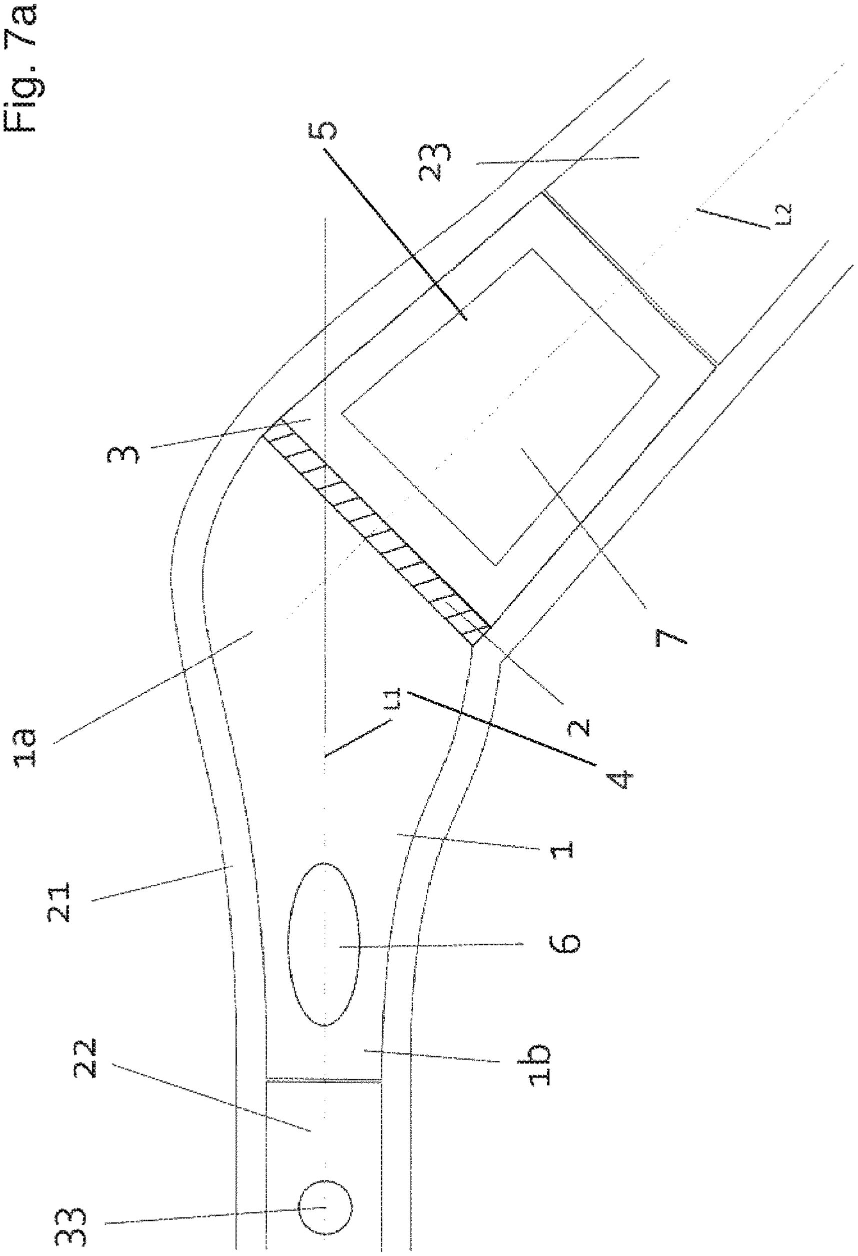
Figure 7B:
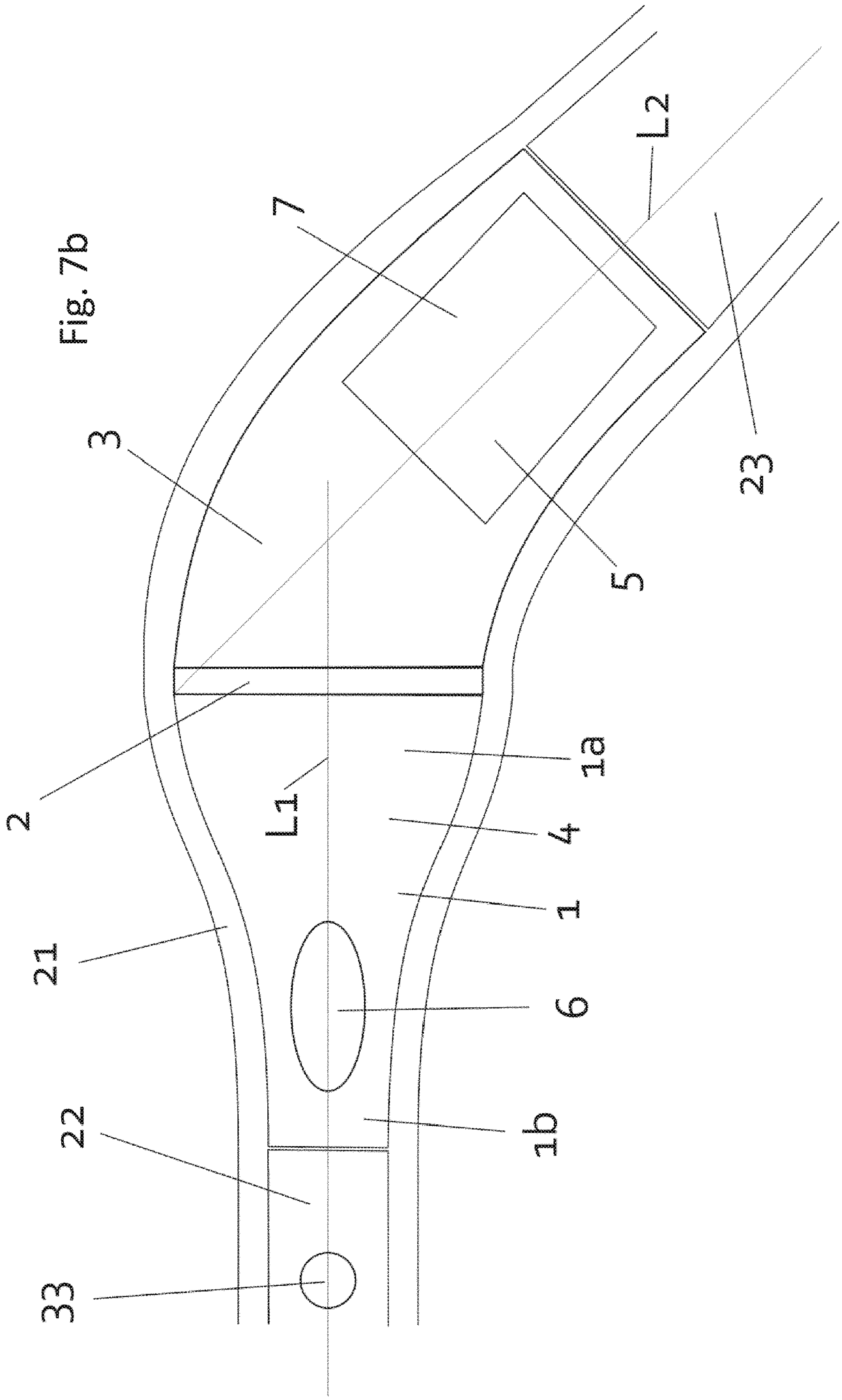
Figure 8:
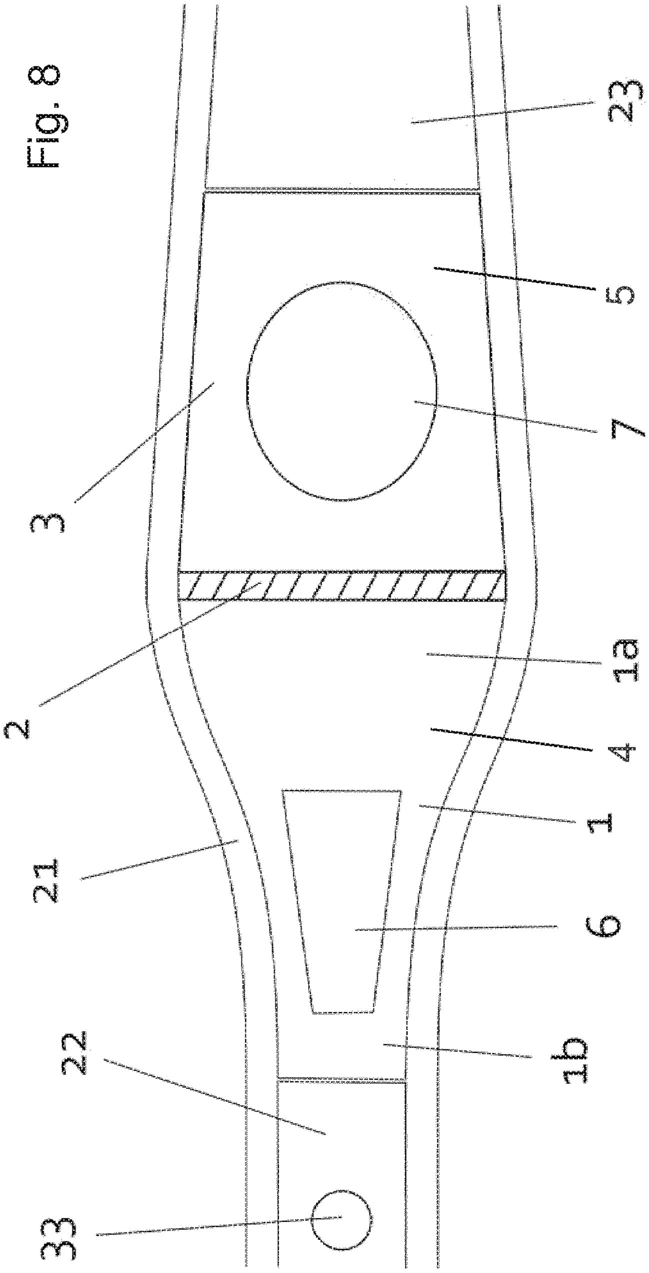
Figure 9:
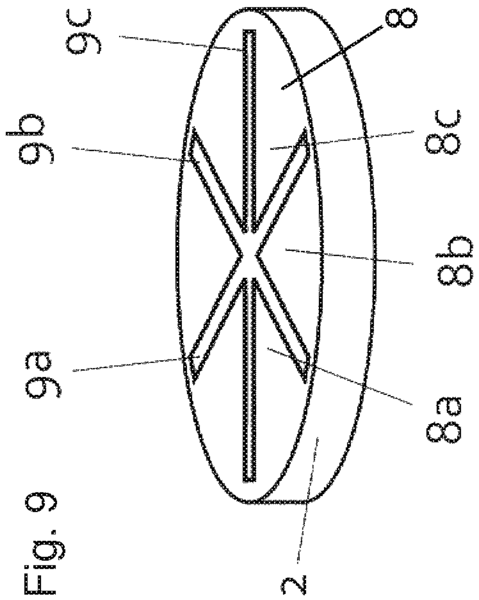
Figure 10:
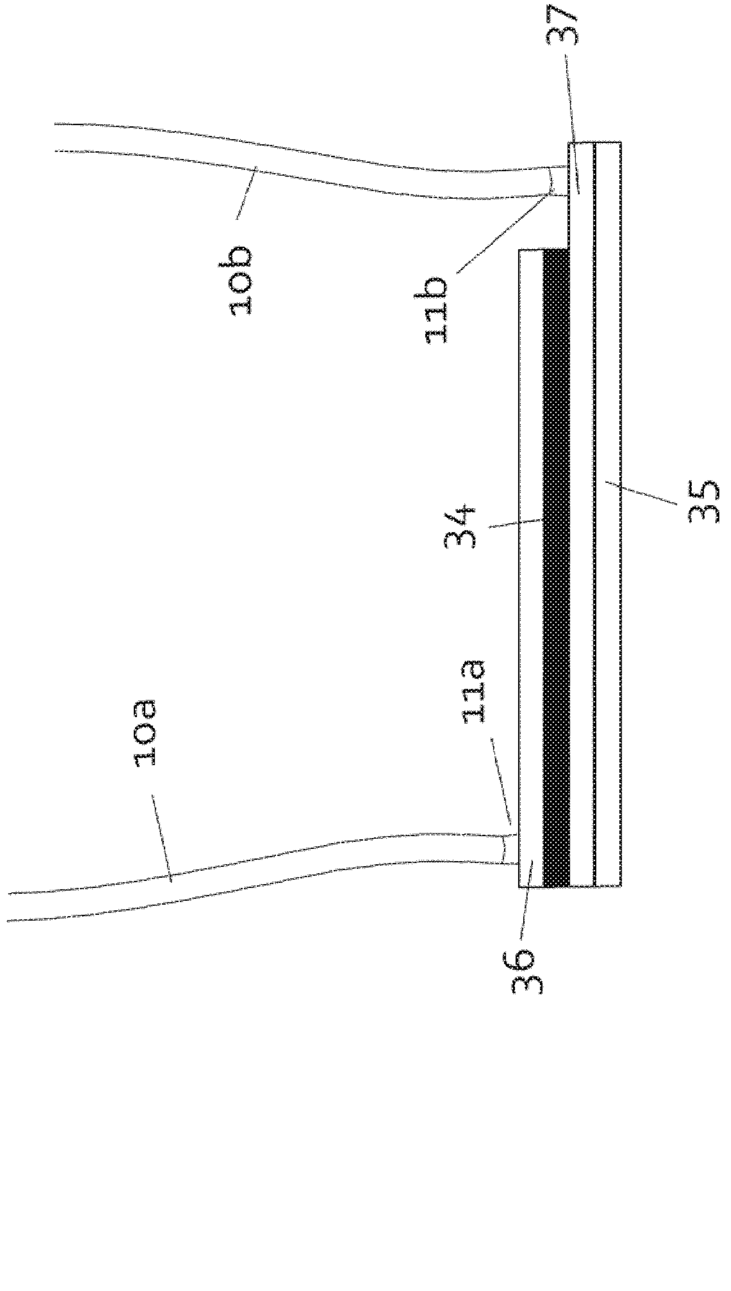
Figure 11:
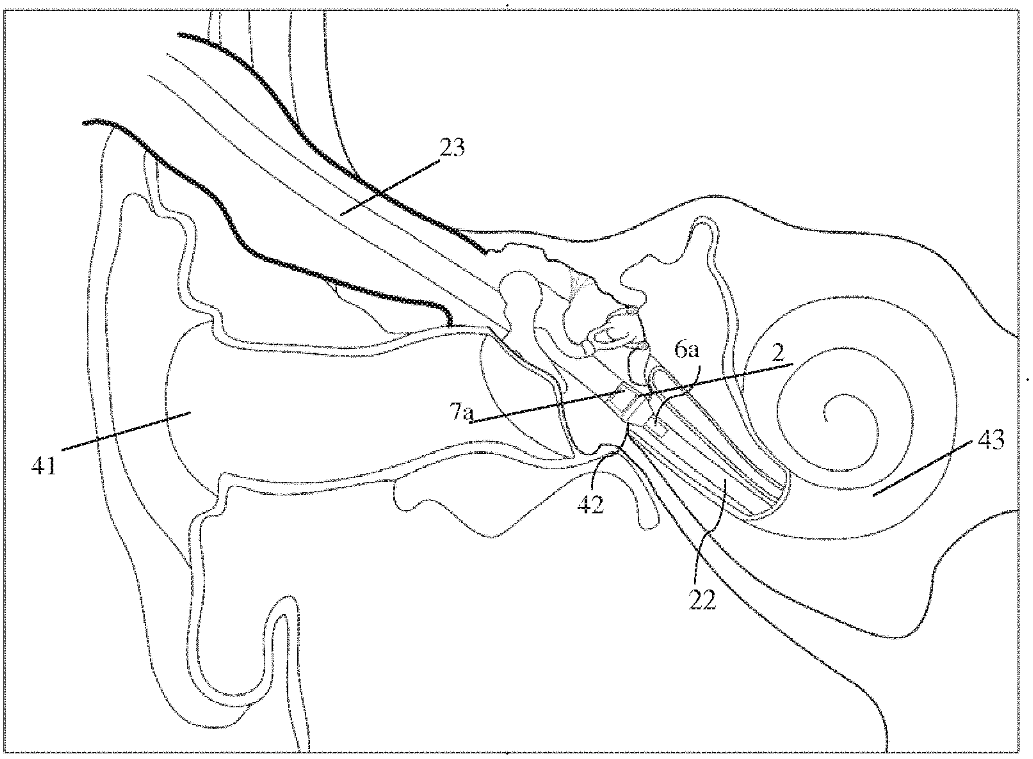

As shown in:

FIG. 1: a side view of an electroacoustic transducer according to the invention, FIG. 2: a view of the electroacoustic transducer shown in FIG. 1, in a viewing direction perpendicular to the viewing direction indicated in FIG. 1, FIGS. 3 to 8: further embodiments of electroacoustic transducers according to the invention, FIG. 9: an example of a sound transducer for use in the invention, FIG. 10: an example of a contacting of a sound transducer 2, FIG. 11: an arrangement of an electron carrier with an electroacoustic transducer according to the invention in an ear, and FIG. 12: some components of a conventional cochlear implant system in an ear.

FIG. 1 shows a side view of an electroacoustic transducer according to the invention which is suited for implantation in an ear. The electroacoustic transducer shown has an inner ear housing 1, a sound transducer 2, and a middle ear component 3, which is here a middle ear housing 3.

There may be gathered, from left to right in FIG. 1, first an electrode carrier 22, followed to the right by an area of constant cross section 1*b,* followed by a tapering area 1*a* of inner ear housing 1, connecting then to sound transducer 2 on the right, and connected to the same by middle ear housing 3 on the right. On the right, an outer shaft 23 is adjacent to middle ear housing 3.

Electrode carrier 22 has at least one electrode 33, which may be contacted with the surroundings of electrode carrier 22, which is thus exposed on the surface of electrode carrier 22. The electrode carrier here is insertable into a cochlea.

Inner ear housing 1 surrounds an inner ear area 4, which is the interior of inner ear housing 1. Inner ear area 4 is then delimited by sound transducer 2 in the direction of middle ear component 3. Middle ear component 3 is arranged on that side of sound transducer 2 opposite inner ear area 4 of inner ear housing 1.

Inner ear housing 1 has at least one sound transmission window 6, which is incorporated into at least one wall of inner ear housing 1 surrounding inner ear area 4, and through which vibrations are transmittable.

Inner ear housing 1 is thereby dimensioned so that it is insertable into an opening between a middle ear and an inner ear of a person, such that inner ear area 4 projects at least partially into the inner ear so that the at least one sound transmission window 6 is located in the inner ear. Middle ear component 3 is preferably configured so that it preferably has a mechanical impedance, which is lower than that of the inner ear area 4, for frequencies in a frequency range that humans are able to hear.

In the example shown, inner ear housing 1 has an area 1*a,* adjacent to sound transducer 2 and which tapers away from sound transducer 2 in the direction of longitudinal axis L of inner ear housing 1. This tapering area 1*a* is adjacent to a cylindrical part 1*b* of inner ear housing 1, in which a diameter of inner ear housing 1 remains constant along longitudinal axis L of inner ear housing 1.

Middle ear housing 3 is arranged on a side of sound transducer 2 opposite inner ear area 4. Middle ear housing 3 surrounds a middle ear area 5 in the example shown. Middle ear area 5 is thereby delimited on one side by sound transducer 2.

The entire arrangement made from electrode carrier 22, inner ear housing 1, sound transducer 2, middle ear housing 3, and outer shaft 23 is surrounded in FIG. 1 by a sleeve material 21, which may have or comprise silicone, for example. Sleeve material 21 may be advantageously applied so that it produces or reinforces a mechanical connection between inner ear housing 1 and electrode carrier 22.

In the example shown in FIG. 1, a wire 26 is incorporated in sleeve material 21 and is electrically connected to the at least one electrode 33 of electrode carrier 22. Wire 26 runs from the at least one electrode 33 in sleeve material 21 up to outer shaft 23 and then along outer shaft 23, for example, to a control electronics, via which a voltage is able to be applied to electrode 33. In the example shown in FIG. 1, sleeve material 21 forms the surface of the entire electroacoustic transducer and thus the surface of middle ear housing 3, inner ear housing 1, and electrode carrier 22. Outer shaft 23 also has sleeve material 21 as a surface. The electroacoustic transducer is thus completely encapsulated in sleeve material 21. However, electrodes 33 of electrode carrier 22 are exposed.

In the example shown in FIG. 1, sound transmission window 6 in inner ear housing 1 has an oval shape. Sound transmission window 7 in middle ear housing 3 has a trapezoidal shape, whose 2 parallel sides lie in parallel to the surface of sound transducer 2, and whose two non-parallel sides are determined by the widening shape of middle ear housing 3 in the direction of the sound transducer.

Both inner ear housing 1 and also middle ear housing 3 may have circular cross sections in planes perpendicular to the drawing plane in the example shown. Starting from the left in the example shown in FIG. 1, the radius of this circular cross section is initially constant in the area of electrode carrier 22, then remains constant in area 1*b* of inner ear housing 1 with a constant cross section, enlarges then in area 1*a* of inner ear housing 1, reaches its maximum at sound transducer 2, and decreases in the example shown at a constant rate in the area of middle ear housing 3 and outer shaft 23 connecting thereto. The radius may transition again into a constant section over the further course of shaft 23. Reference is made to the fact that the described course of the radius is optional.

Inner ear housing 1 in the area of the at least one sound transmission window 6 may advantageously have a lower mechanical impedance than in the area outside of the at least one sound transmission window 6. This may correspondingly apply for sound transmission window 7 in middle ear housing 3.

In the example shown in FIG. 1, sound transducer 2 extends in a plane which lies parallel to or tilted at an angle of less than 45° to a plane which is perpendicular to longitudinal axis L of inner ear housing 1 and/or of middle ear housing 3 (see also FIGS. 7*a* and 7*b*).

In FIG. 1, the at least one sound transmission window 6 is provided in a side wall of the inner ear housing surrounding a longitudinal axis of inner ear area 4 and/or is provided in a side wall delimiting inner ear area 4 on a side facing away from sound transducer 2 in the direction of longitudinal axis L of inner ear area 4.

In one exemplary embodiment of the invention, sleeve material 21 may be identical to the vibration transmission material and in particular may materially transition into the same.

Inner ear housing 1 and, in particular conical area 1*a* may advantageously have a section in which its diameter, perpendicular to longitudinal axis L of the inner ear housing, is greater than its diameter at that point, at which inner ear housing 1 comes to lie in an opening between a middle ear and the inner ear of the person in the implanted state. That area of inner ear housing 1 facing sound transducer 2 then has a larger diameter, and that area of inner ear housing 1 facing away from sound transducer 2 has a smaller diameter than the extension of the corresponding opening. In particular, the diameter of cylindrical part 1*b* is advantageously smaller than the smallest dimension of the abovementioned opening between the middle ear and inner ear, such that cylindrical part 1*b* of the inner ear housing may be guided through the opening between the middle ear and inner ear.

In one advantageous embodiment of the invention, inner ear area 4 may be at least partially filled with a vibration transmission material. The vibration transmission material may thereby contact sound transducer 2 and sound transmission window 6 such that vibrations are transmittable from sound transducer 2 to windows 6 via the vibration transmission material. Such a vibration transmission material may preferably be a solid with a modulus of elasticity lower than a modulus of elasticity of inner ear housing 1, or may be a fluid with a suitable compression modulus.

Middle ear component 3 may also have a medium which contacts sound transducer 2. In particular, middle ear housing 3 may be filled with this medium in middle ear area 5. Advantageously, the medium may be a solid whose modulus of elasticity is lower than the modulus of elasticity of inner ear housing 1 and/or middle ear housing 3. The solid may, for example, have or be silicone.

It is also possible that middle ear area 5 contains a solid, liquid, or gaseous medium, which contacts sound transducer 2 and causes a lower mechanical impedance, at least in a frequency which humans are able to hear, than a vibration transmission material with which inner ear area 4 may be filled. If the medium is a fluid, then its modulus of compression may be greater than or equal to 0.1 GPa for example.

In the example shown in FIG. 1, a surface of sound transducer 2 extends in a plane which is parallel to a plane to which longitudinal axis L of inner ear housing 1 is perpendicular. The surface of sound transducer 2 is thus perpendicular to longitudinal axis L of inner ear housing 1 and middle ear housing 3. This arrangement is not essential. It is, however, advantageous if sound transducer 2 is arranged in this way or is tilted at an angle of less than 45° to the stated plane, to which longitudinal axis L of inner ear housing 1 or of the middle ear housing is perpendicular.

In the example shown in FIG. 1, sound transducer 2, as shown by way of example in FIG. 10, may be configured as a membrane structure, which may have, for example, a carrier layer 35 and a piezoelectric layer 34 arranged on carrier layer 35, wherein piezoelectric layer 34 may have at least one piezoelectric material, such that vibrations of membrane structure 2 may be generated by applying a voltage to piezoelectric layer 34.

In the examples shown here, a minimal diameter of inner ear housing 1 may be less than or equal to 3 mm and/or greater than or equal to 0.3 mm. A length of inner ear housing 1 in the direction of longitudinal axis L may, for example, be less than or equal to 3 mm and/or greater than or equal to 1 mm. A diameter of the sound transducer may, for example, be less than or equal to 5 mm and/or greater than or equal to 0.8 mm. A length of middle ear housing 3 in the direction of longitudinal axis L may, for example, be less than or equal to 2 mm and/or greater than or equal to 1 mm.

The opening, into which the electroacoustic transducer according to the invention is insertable, may be, for example, a round window or an oval window of a person, or an opening created between the middle ear and the inner ear, which is introduced by a doctor.

Sound transducer 2 may advantageously be an actuator which generates vibrations when an electric voltage is applied. However, it is also possible that the sound transducer is designed to generate an electric voltage from an acoustic signal. Such a voltage may then be used, for example, to generate a voltage which may be applied to the electrodes of electrode carrier 22 after corresponding amplification. This voltage, which may be applied to the electrodes, is then controlled by the voltage generated by sound transducer 2.

FIG. 2 shows the electroacoustic transducer shown in FIG. 1 in a view rotated by 90° about a longitudinal axis L of the transducer. Sound transmission window 6 in inner ear area 4 and sound transmission window 7 in middle ear housing 3 are shown from the side in the view in FIG. 2. In the example shown in FIG. 2, sound transmission window 6 in inner ear area 4 has a flexible membrane 24, by means of which inner ear area 4 is separated with respect to a surroundings of the electroacoustic transducer. In addition, sound transmission window 7 in middle ear area 5 is sealed by means of a flexible membrane 25, which delimits middle ear area 5 with respect to the surroundings of the electroacoustic transducer. Both membrane 24 and also membrane 25 are configured in the example shown so that sound vibrations are transmittable by them.

In one optional embodiment, membranes 24 and 25 may be configured as part of sleeve material 21. The flexible membrane may then partially or completely cover the surface of electrode carrier 22 and also that of inner ear housing 1 and of middle ear housing 3, such that described membranes 24 and 25 are partial areas of this membrane.

Figure 3:
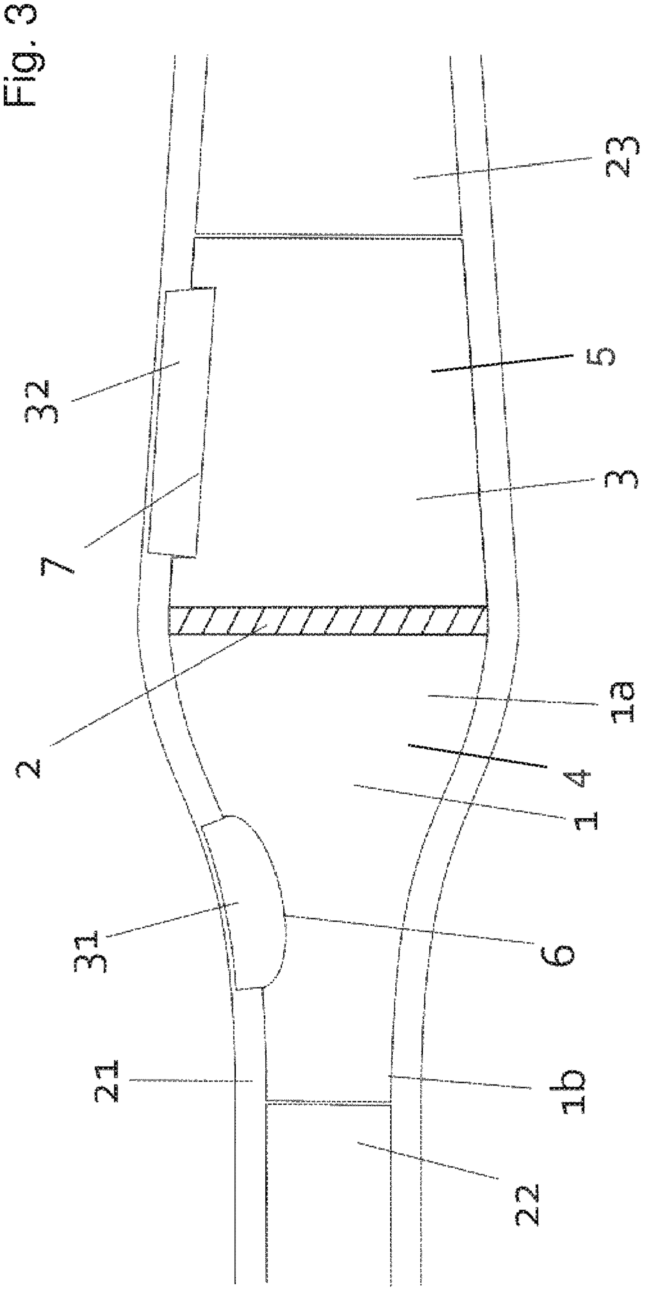

FIG. 3 shows another example of an embodiment of the invention. Aside from the subsequently described differences, the embodiment in this example corresponds to that shown in FIGS. 1 and 2, such that reference is made to the description there.

In FIG. 3, at least one segment 31 is incorporated in sound transmission window 6 in inner ear housing 1 and comprises or consists of a vibration transmission material. In the example shown in FIG. 3, at least one segment 32 is also incorporated in sound transmission window 7 in middle ear housing 3 and comprises or consists of a vibration transmission material. The corresponding window may be sealed by segments 31 and 32. The at least one segment 31 in sound transmission window 6 and/or the at least one segment 32 in sound transmission window 7 are thereby advantageously shaped in such a way that their surface corresponds to the surface of sleeve material 21 or is covered by sleeve material 21 by only a film whose film thickness is less than the film thickness of sleeve material 21 in the area outside of sound transmission window 6 and/or of sound transmission window 7.

Figure 4:
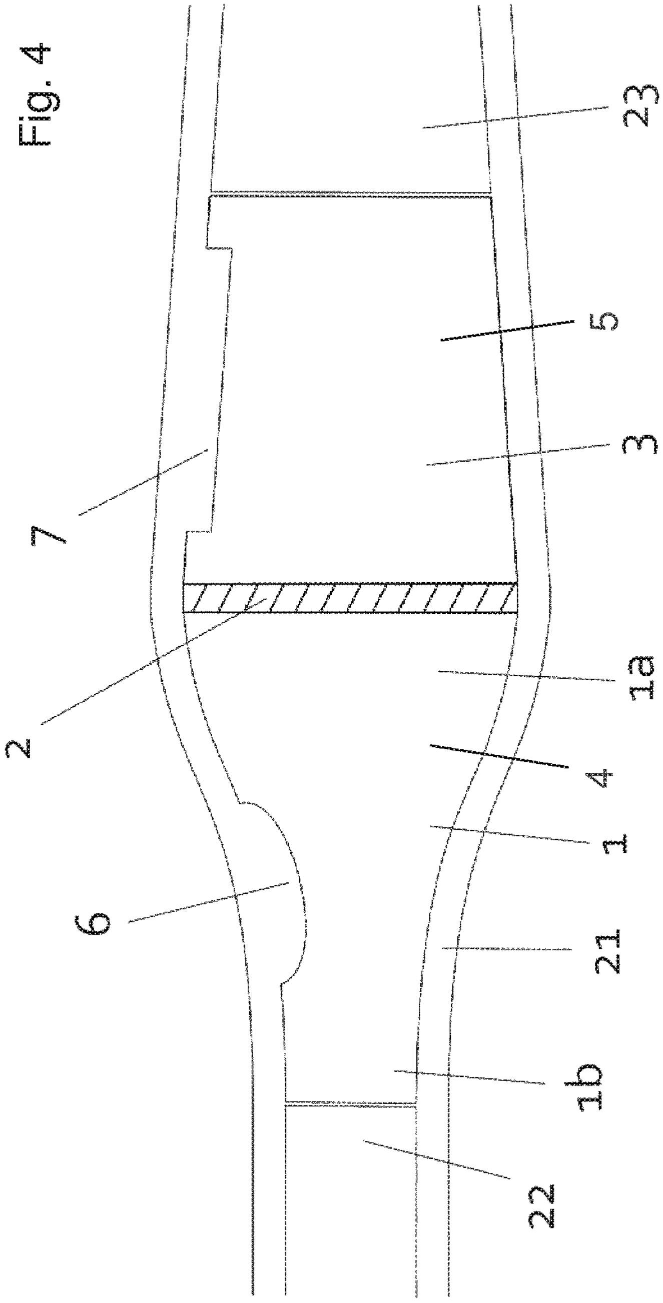

FIG. 4 shows another embodiment of the invention. This is, aside from the subsequently described differences, configured like the embodiment shown in FIGS. 1 and 2.

Sound transmission window 6 in FIG. 4 is an opening in inner ear housing 1, through which the sound transmission material extends which is simultaneously the material of sleeve 21. Sound transmission window 3 in middle ear housing 3 is correspondingly configured as an opening in middle ear housing 3, through which the sound transmission material extends which is also sleeve material 21.

Figure 5:
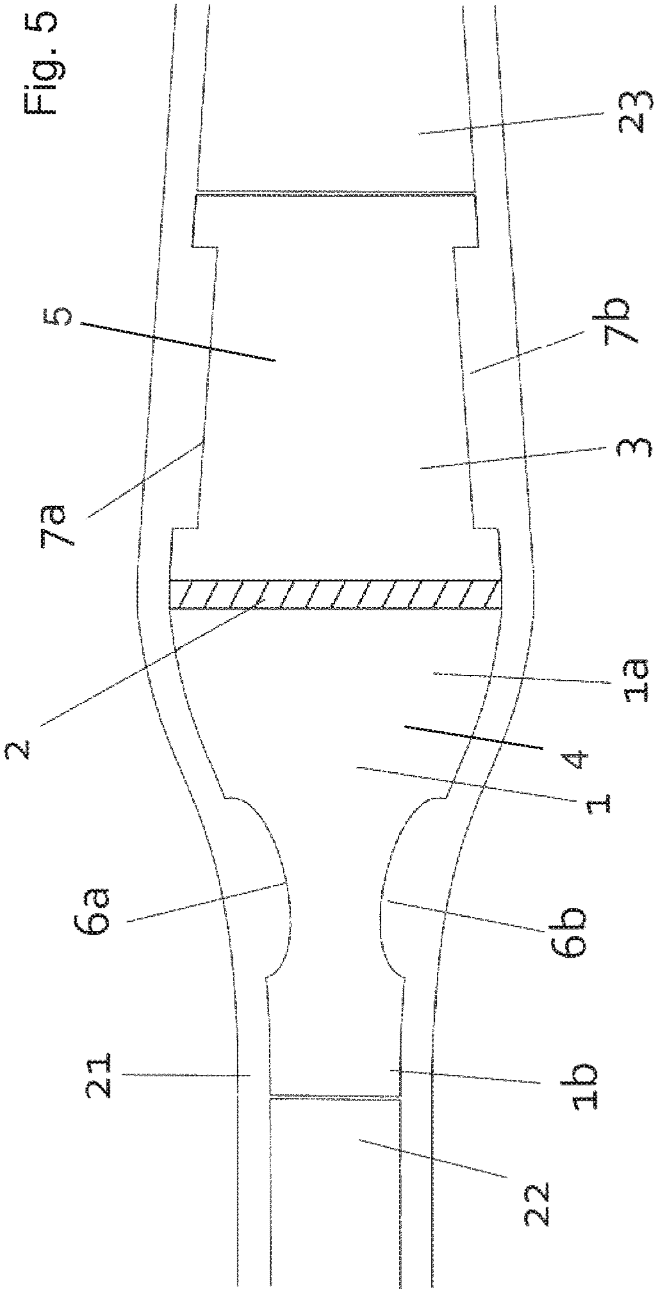

FIG. 5 shows another exemplary embodiment of an electroacoustic transducer according to the invention. In the example shown in FIG. 5, inner ear housing 12 has two sound transmission windows 6*a,* and 6*b* which lie opposite one another with respect to longitudinal axis L of inner ear housing 1. The shape of sound transmission windows 6*a* and 6*b* is respectively identical to the shape of sound transmission window 6 shown in FIG. 1; however, it may also deviate from the same.

In addition, in the example shown in FIG. 5, middle ear housing 3 has two sound transmission windows 7*a* and 7*b* lying opposite one another with respect to longitudinal axis L of middle ear housing 3, whose shape is respectively identical to that of sound transmission window 7 shown in FIG. 1; however, it may also deviate from the same.

As in the example shown in FIG. 5, both sound transmission windows 6*a* and 6*b* in inner ear housing 1 and also sound transmission windows 7*a* and 7*b* in middle ear housing 3 are configured as openings, through which the sound transmission material extends, which is simultaneously the material of sleeve 21.

Figure 6:
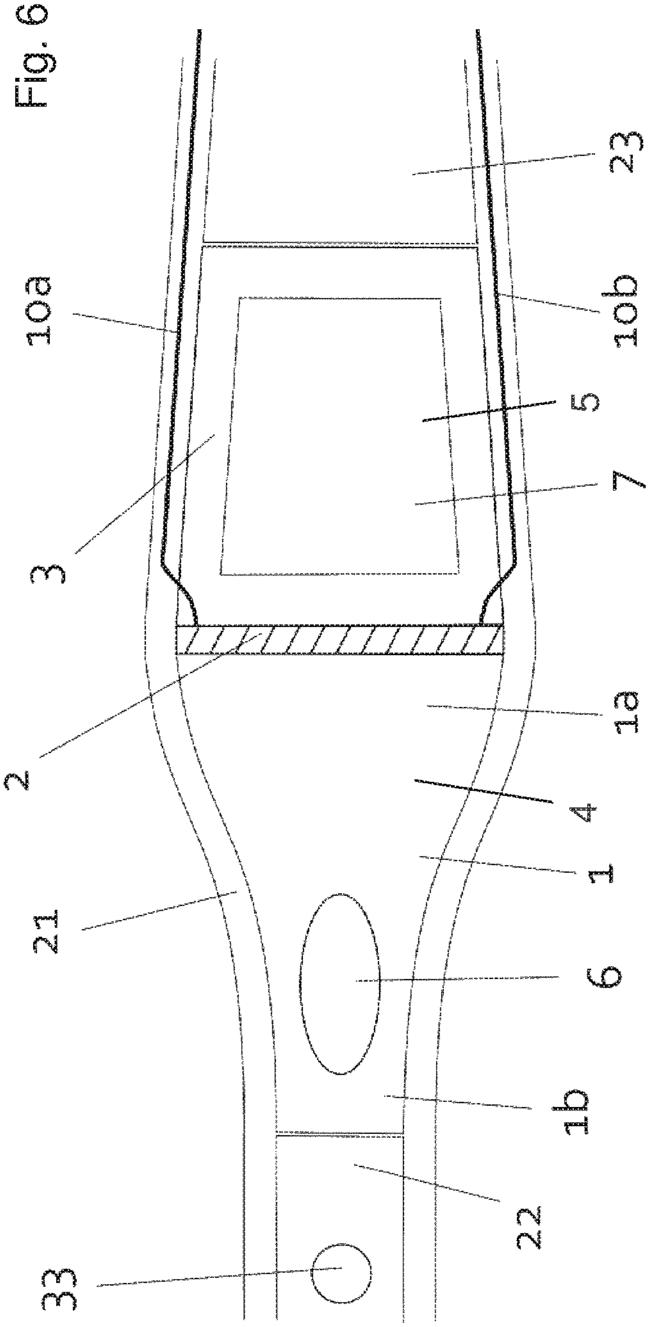

FIG. 6 shows another exemplary embodiment of the invention. Insofar as nothing is subsequently described differently, the configuration of this example is identical to that shown in FIG. 1.

In the example shown in FIG. 6, two electrical lines 10*a* and 10*b* are provided, by means of which sound transducer 2 is electrically contactable. Like wire 26, electrical lines 10*a* and 10*b* are embedded in sleeve material 21. Lines 10*a* and 10*b* initially run along outer shaft 23 and then in sleeve material 21 along middle ear housing 3 up to sound transducer 2 and end at the same in order to electrically contact it.

Wire 26 for contacting the at least one electrode 33 may be provided here as shown in FIG. 1. However, the method for contacting sound transducer 2 is independent of the method for contacting electrode 33 of electrode carrier 22, such that other possibilities for the contacting of electrode 33 in FIG. 6 may also be realized.

In the example shown, electrical lines 10*a*, 10*b* run in sleeve material 21 outside of inner ear housing 1 and middle ear housing 3 in the direction of a longitudinal axis L from one side of the electroacoustic transducer to an opposite side of the electroacoustic transducer. Longitudinal axis L of the electroacoustic transducer should thereby be understood as an axis which extends coaxially to longitudinal axis L of inner ear housing 1 and/or a longitudinal axis L of middle ear housing 3. In the example shown, this is one axis, to which the surface of sound transducer 2 is perpendicular and about which inner ear housing 1 and middle ear housing 3 are symmetrical at least in sections in the example shown. Two electrical lines 10*a* and 10*b* lie here radially opposite one another with respect to longitudinal axis L, which is, however, optional. Electrical lines 10*a* and 10*b* may be configured here as ribbon cables, which lie flat on an outer side of the electroacoustic transducer. Electrodes of an electrode carrier connecting to inner ear area 4, not shown in the figure, may be electrically contacted by means of lines 10*a* and 10*b*.

FIG. 7*a* shows an exemplary embodiment of the invention, whose components match those shown in FIG. 1. However, while the electroacoustic transducer of the invention in FIG. 1 is configured as straight, thus has a straight symmetrical axis, the embodiment shown in FIG. 7 has an angled shape. The angulation is thereby achieved by the configuration of tapering area 1*a* of inner ear housing 1. As a result, a longitudinal axis L1 of electrode carrier 22 is at an angle to longitudinal axis L2 of middle ear housing 3, longitudinal axis L1 of electrode carrier 22 and L2 of middle ear housing 3 are thus not parallel and not coaxial. In this embodiment, longitudinal axis L2 of the middle ear housing extends perpendicular to a surface in which sound transducer 2 extends.

In an alternative configuration of this embodiment, as is shown in FIG. 7*b*, the angulation may be achieved by the configuration of middle ear housing 3. In this case, longitudinal axis L1 of electrode carrier 22 or of inner ear area 4 extends perpendicular to the surface in which sound transducer 2 extends.

FIG. 8 shows another exemplary embodiment of an electroacoustic transducer according to the invention. Aside from the subsequently described differences, this embodiment is again configured identically to the embodiment shown in FIG. 1.

In FIG. 1, sound transmission window 6 in inner ear housing 1 has an oval shape. In contrast, sound transmission window 6 in FIG. 8 has a trapezoidal shape.

In addition, sound transmission window 7 in middle ear housing 3 has a trapezoidal shape in FIG. 1. In contrast, sound transmission window 7 in middle ear housing 3 has an oval or elliptical shape in the example shown in FIG. 8. A circular shape is also possible.

The shapes of sound transmission windows 6 and 7, shown in FIGS. 1 and 8, may be combined arbitrarily with one another, such that both sound transmission window 6 in inner ear housing 1 and sound transmission window 7 in middle ear housing 3 may have a trapezoidal shape or both sound transmission window 6 and also sound transmission window 7 may have a circular or elliptical shape, or any other arbitrary shape.

FIG. 9 shows an example of a sound transducer 2, as may be used in the electroacoustic transducer according to the invention.

In the example shown, sound transducer 2 has a circular periphery. In general, the peripheral shape of sound transducer 2 is preferably identical to the peripheral shape of inner ear housing 1 and middle ear housing 3. In the example shown in FIG. 9, sound transducer 2 has a membrane structure 8 which is delimited by a circular edge.

The membrane structure is thereby divided by cut lines 9*a*, 9*b*, and 9*c* into segments 8*a*, 8*b*, and 8*c*, among other things. Cut lines 9*a*, 9*b*, and 9*c* are thereby configured so that they sever all layers of membrane structure 8. Segments 8*a*, 8*b*, and 8*c* are thus mechanically decoupled at cut lines 9*a*, 9*b*, and 9*c*. Segments 8*a*, 8*b*, and 8*c* are permanently arranged on the edge at their outer edges. Segments 8*a*, 8*b*, and 8*c* thus have a pie wedge shape and are deflectable at their points.

The membrane structure may thereby have a carrier layer and at least one piezoelectric layer arranged on the carrier layer and having at least one piezoelectric material, such that vibrations of the membrane structure are generatable by applying a voltage to the piezoelectric layer.

In the example shown in FIG. 9, segments 8*a*, 8*b*, and 8*c* therefore vibrate with their points facing the center of the circular shape due to the application of such a voltage.

The membrane structure of sound transducer 2 is divided, in the example shown, into six segments, like segments 8*a*, 8*b*, and 8*c* by way of example, in the surface of the membrane structure by cut lines 9*a*, 9*b*, 9*c*, which sever all layers of the membrane structure, such that the membrane structure is mechanically decoupled at cut lines 9*a*, 9*b*, 9*c*. In the example shown, the cut lines run radially to a center point of sound transducer 2 and meet at the center point, such that all segments are mechanically decoupled at the center point, like segments 8*a*, 8*b*, and 8*c* by way of example. Reference is explicitly made to the fact that the number of segments, like segments 8*a*, 8*b*, and 8*c* by way of example, the number of cut lines 9*a*, 9*b*, 9*c*, and also the shape of cut lines 9*a*, 9*b*, 9*c* and segments, like segments 8*a*, 8*b*, and 8*c* by way of example, may be realized in multiple other ways. For example, spiral shaped cut lines are also possible.

FIG. 10 shows, by way of example, one possibility for contacting sound transducer 2 by means of two wires 10*a* and 10*b*. For example, the contacting of sound transducer 2, shown in FIG. 6, may be configured by means of these wires, as shown in FIG. 10.

Sound transducer 2 has a carrier layer 35 on which a back electrode 37 is arranged. Carrier layer 35 is hereby configured as flat with a shape corresponding to the shape of sound transducer 2, preferably a circular shape. In the example shown, back electrode 37 is arranged with a parallel surface directly on carrier layer 35.

A piezoelectric layer 34, which in the example shown is configured as flat and with a parallel surface lying directly on the back electrode 37, is arranged on that side of back electrode 37 facing away from carrier layer 35.

In addition, a likewise flat front electrode 36, which completely covers piezoelectric layer 34 and is here likewise arranged directly on piezoelectric layer 34, is arranged on that side of piezoelectric layer 34 facing away from back electrode 37.

Wire 10 is connected to front electrode 36 via a terminal 11*a* for electrical contacting of sound transducer 2. In addition, wire 10*b* is electrically connected to back electrode 37 via a terminal 11*b*.

FIG. 11 shows an electroacoustic transducer, as configured in FIGS. 1 to 8 by way of example, inserted into an ear 41 of a person. The electroacoustic transducer is thereby guided through a round window 42 in the ear of the person and arranged so that round window 42 lies at the height of conical area 1*b* of inner ear housing 1. Electrode carrier 22 with at least one electrode 33 is thereby inserted into cochlea 43 of the person. Outer shaft 23 preferably runs through the mastoid of the cranial bone. It contains the electrically conducting connection of electrode 33 to the electronics for controlling stimulation pulses of the cochlear implant system. The electronics for controlling stimulation pulses are generally installed in a housing, sealed as closely as hermetically possible, which lies subcutaneously behind the ear (not depicted in FIG. 11). Outer shaft 23 may, for example, be created by means of a surgical intervention (e.g., mastoidectomy) from the cranial bone behind the ear to the middle ear through the temporal bone.

FIG. 12 shows a typical human ear with an outer ear 101, an eardrum 102, middle ear 103, inner ear 104, and auditory nerve 113. In addition, typical components of a cochlear implant system are schematically depicted: external processing unit 111, transmission coil 107 for sending or receiving energy and signals between external and implanted components, implant 108 with integrated or externally connected transmission coil for sending or receiving energy and signals between external and implanted components, electrode lead 109 (shaft 23 in other figures), electrode carrier 110 (22 in other figures), and electrode contact 112 (33 in other figures) .

The invention claimed is:

1. An electroacoustic transducer for implantation into an ear, comprising:

an inner ear housing;

at least one sound transducer; and a middle ear component;

wherein the middle car component has a middle ear housing enclosing a middle ear area, wherein the inner ear housing surrounds an inner ear area, which is adjacent to the at least one sound transducer and delimited by the at least one sound transducer, wherein the middle ear component is arranged on a side of the at least one sound transducer opposite the inner ear area, wherein the inner ear housing has at least one sound transmission window, which is incorporated into at least one wall of the inner ear housing, and through which vibrations may be transmitted, and wherein the inner ear housing is configured so that it is insertable into an opening between a middle ear and an inner ear of a person, such that the inner ear area projects at least partially into the inner ear so that the at least one sound transmission window is located in the inner ear, and wherein a mechanical impedance of the inner ear area is greater than a mechanical impedance of the middle ear area, for one or more frequencies in a frequency range that is audible to a human ear.

2. The electroacoustic transducer according to claim 1, wherein, when the electroacoustic transducer is inserted into its intended position between the inner ear and a middle ear of a person, the mechanical impedance of the inner ear area is greater than the mechanical impedance of the middle ear area, for one or more frequencies in a frequency range that is audible to the human ear.

3. The electroacoustic transducer according to claim 1, wherein the middle ear component has a medium which contacts the at least one sound transducer, wherein the medium is a solid with a modulus of elasticity that is lower than a modulus of elasticity of the inner ear housing, wherein the modulus of elasticity of the solid is less than or equal to 10% of the modulus of elasticity of the inner ear housing, and wherein the solid comprises silicone.

4. The electroacoustic transducer according to claim 1, wherein the middle ear area is delimited on one side by the at least one sound transducer.

5. The electroacoustic transducer according to claim 4, wherein the middle ear housing has at least one window which is incorporated in a wall of the middle ear housing.

6. The electroacoustic transducer according to claim 4, wherein the middle ear housing is formed at least partially from at least one wire and a sheath surrounding the at least one wire, wherein the at least one wire and the sheath are mechanically connected to one another.

7. The electroacoustic transducer according to claim 4, wherein the middle ear housing tapers along a longitudinal axis of the middle ear area in a direction away from the at least one sound transducer.

8. The electroacoustic transducer according to claim 4, further comprising:

an electrode carrier, wherein at least one of the inner ear housing, the middle ear housing, or the electrode carrier is at least partially coated on an outer side or surrounded by a sleeve material.

9. The electroacoustic transducer according to claim 8, wherein the sleeve material includes a silicone.

10. The electroacoustic transducer according to claim 8, wherein the sleeve material is applied in such a way that it produces or reinforces a mechanical connection between the inner ear housing and the electrode carrier.

11. The electroacoustic transducer according to claim 8, wherein at least one of the sleeve material or the inner ear housing has at least one channel on an outer side and/or the middle ear housing has at least one channel on an outer side in which at least one wire runs in a direction of a longitudinal axis of the inner ear housing or of the middle ear housing, and wherein the at least one wire electrically contacts at least one electrode of the electrode carrier.

12. The electroacoustic transducer according to claim 8, wherein the sleeve material has at least one segment for sealing the at least one sound transmission window in an area of the at least one sound transmission window, wherein the at least one segment comprises a vibration transmission material, wherein the vibration transmission material is a solid with a modulus of elasticity that is lower than a modulus of elasticity of the inner ear housing, wherein the modulus of elasticity of the solid is less than or equal to 10%, of the modulus of elasticity of the inner ear housing, and wherein the solid comprises silicone.

13. The electroacoustic transducer according to claim 4, wherein at least one of the inner ear housing or the middle ear housing is produced from at least one of: a plastic material, polyimide, PEEK, polyamide, silicone, epoxy resin, PET, metal, metal alloy, gold, platinum, titanium, titanium alloy, aluminum, ceramic, glass, quartz glass, zirconium oxide, aluminum oxide, or a combination thereof.

14. The electroacoustic transducer according to claim 4, wherein a minimum diameter of the inner ear housing is less than or equal to 3 mm, wherein a length of the inner ear housing is less than or equal to 30 mm, wherein a diameter of the at least one sound transducer is less than or equal to 5 mm and wherein a length of the middle ear housing is less than or equal to 20 mm.

15. The electroacoustic transducer according to claim 1, wherein the inner ear housing has a smaller minimum diameter in a direction perpendicular to a longitudinal axis of the inner ear housing than the middle ear component.

16. The electroacoustic transducer according to claim 1, having at least one, electrical line which is located outside of the inner ear housing and the middle ear component from one side of the electroacoustic transducer in a direction of a longitudinal axis of the electroacoustic transducer to an opposite side in the direction of the longitudinal axis of the electroacoustic transducer.

17. An electroacoustic transducer for implantation into an ear, comprising:

an inner ear housing;

at least one sound transducer; and an electrode carrier with at least one electrode arranged on a surface of the electrode carrier;

wherein the inner ear housing surrounds an inner ear area, which is adjacent to the at least one sound transducer and delimited by the at least one sound transducer, wherein the inner ear housing has at least one sound transmission window, which is incorporated into at least one wall of the inner ear housing, and through which vibrations may be transmitted, wherein the inner ear housing is configured such that it is insertable into an opening between a middle ear and an inner ear of a person, such that the inner ear area projects at least partially into the inner ear such that the at least one sound transmission window is located in the inner ear, and wherein the electrode carrier extends from the inner ear area in a direction away from the at least one sound transducer, wherein the inner ear area is at least partially filled with a vibration transmission material, so that the vibration transmission material contacts at least one of the at least one sound transducer or the at least one sound transmission wind ow, wherein the vibration transmission material is a solid with a modulus of elasticity that is lower than a modulus of elasticity of the inner ear housing, and wherein the modulus of elasticity of the solid is less than or equal to 10% of the modulus of elasticity of the inner ear housing.

18. The electroacoustic transducer according to claim 17, wherein a surface of the electroacoustic transducer or of the electrode carrier comprises the vibration transmission material.

19. A cochlear implant system, comprising:

at least one microphone;

at least one battery;

at least one processor unit;

at least one electronic component for generating a stimulation pulse; and an electroacoustic transducer, the electroacoustic transducer comprising:

an inner ear housing;

at least one sound transducer, wherein the inner ear housing surrounds an inner ear area located adjacent to the at least one sound transducer and delimited by the at least one sound transducer;

a middle ear component, wherein the middle ear component includes a middle ear housing enclosing a middle ear area, and wherein a mechanical impedance of the inner ear area is greater than a mechanical impedance of the middle ear area for one or more frequences in a frequency range that is audible to a human ear; and an electrode carrier with at least one electrode arranged on a surface of the electrode carrier.

* * * * *